(12) United States Patent
Davies et al.

(10) Patent No.: US 7,786,107 B2
(45) Date of Patent: Aug. 31, 2010

(54) MODULATORS OF MUSCARINIC RECEPTORS

(75) Inventors: Robert J. Davies, Somerville, MA (US); Jinwang Xu, Framingham, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 276 days.

(21) Appl. No.: 11/894,092

(22) Filed: Aug. 20, 2007

(65) Prior Publication Data

US 2010/0063021 A9    Mar. 11, 2010

Related U.S. Application Data

(60) Provisional application No. 60/838,701, filed on Aug. 18, 2006.

(51) Int. Cl.
     C07D 487/10      (2006.01)
     C07D 487/20      (2006.01)
     C07D 519/00      (2006.01)
     A61K 31/55      (2006.01)

(52) U.S. Cl. .................. 514/212.02; 540/495; 540/543
(58) Field of Classification Search ................ 540/495, 540/543; 514/212.02
See application file for complete search history.

(56) References Cited

U.S. PATENT DOCUMENTS

| | | | |
|---|---|---|---|
| 3,654,287 A | 4/1972 | Dykstra | |
| 3,666,764 A | 5/1972 | Campbell et al | |
| 3,959,475 A | 5/1976 | Bauer et al. | |
| 3,962,259 A | 6/1976 | Bauer et al. | |
| 4,233,307 A | 11/1980 | Ono et al. | |
| 4,349,549 A | 9/1982 | Roszkowski | |
| 4,558,049 A | 12/1985 | Bernardi et al. | |
| 4,612,121 A | 9/1986 | Hermansson | |
| 5,091,387 A | 2/1992 | Evans et al. | |
| 5,219,860 A | 6/1993 | Chambers et al. | |
| 5,324,733 A | 6/1994 | Billington et al. | |
| 5,457,207 A | 10/1995 | Efange et al. | |
| 5,536,716 A | 7/1996 | Chen et al. | |
| 5,576,321 A | 11/1996 | Krushinski et al. | |
| 5,578,593 A | 11/1996 | Chen et al. | |
| 5,614,523 A | 3/1997 | Audia et al. | |
| 5,627,196 A | 5/1997 | Audia et al. | |
| 5,652,235 A | 7/1997 | Chen et al. | |
| 5,658,921 A | 8/1997 | Perregaard et al. | |
| 5,665,725 A | 9/1997 | Moltzen et al. | |
| 5,693,643 A | 12/1997 | Gilbert et al. | |
| 5,741,789 A | 4/1998 | Hibschman et al. | |
| 5,789,402 A | 8/1998 | Audia et al. | |
| 5,817,679 A | 10/1998 | Shen et al. | |
| 5,885,999 A | 3/1999 | Elliott et al. | |
| 6,013,652 A | 1/2000 | Maccoss et al. | |
| 6,130,217 A | 10/2000 | Arnold et al. | |
| 6,166,040 A | 12/2000 | Fairhurst et al. | |
| 6,294,534 B1 | 9/2001 | Nargund et al. | |
| 6,316,437 B1 | 11/2001 | Hoffman et al. | |
| 6,326,375 B1 | 12/2001 | Fukami | |
| 6,436,962 B1 | 8/2002 | Bock et al. | |
| 6,566,367 B2 | 5/2003 | Bakthavatchalam et al. | |
| 6,713,487 B2 | 3/2004 | Yu et al. | |
| 6,720,324 B2 | 4/2004 | Marzabadi et al. | |
| 6,828,440 B2 | 12/2004 | Goehring et al. | |
| 6,869,960 B2 | 3/2005 | Ito et al. | |
| 6,943,199 B2 | 9/2005 | deLombaert et al. | |
| 7,045,527 B2 | 5/2006 | Chen et al. | |
| 7,205,417 B2 | 4/2007 | Fukami et al. | |
| 7,279,471 B2 | 10/2007 | Mueller et al. | |
| 7,351,706 B2 | 4/2008 | Bissantz et al. | |
| 2002/0188124 A1 | 12/2002 | Fukami et al. | |
| 2003/0036652 A1 | 2/2003 | Bakthavatchalam et al. | |
| 2003/0158219 A1 | 8/2003 | Ito et al. | |
| 2004/0054177 A1 | 3/2004 | Otake et al. | |
| 2004/0072847 A1 | 4/2004 | Bakthavatchalam et al. | |
| 2004/0122074 A1 | 6/2004 | Dow et al. | |
| 2004/0142956 A1 | 7/2004 | Chen et al. | |
| 2004/0204397 A1 | 10/2004 | Chaturvedula et al. | |
| 2005/0033048 A1 | 2/2005 | Bakthavatchalam et al. | |
| 2005/0143372 A1 | 6/2005 | Ghosh et al. | |
| 2005/0153998 A1 | 7/2005 | Ito et al. | |
| 2005/0176703 A1 | 8/2005 | Gabriel et al. | |
| 2005/0215576 A1 | 9/2005 | Degnan et al. | |
| 2005/0261332 A1 | 11/2005 | Distefano et al. | |

(Continued)

FOREIGN PATENT DOCUMENTS

CN      1535967      10/2004

(Continued)

OTHER PUBLICATIONS

Abdel-Magio, A., "Reductive Amination of Aldehydes and Ketones with Sodium Triacetoxyborohydride. Studies on Direct and indirect Reductive Amination Procedures1", J. Org. Chem., 61 (1996), pp. 3849-3862.

(Continued)

*Primary Examiner*—Bruck Kifle
(74) *Attorney, Agent, or Firm*—Honigman Miller Schwartz & Cohn; Jonathan P. O'Brien; Heidi M. Berven

(57) ABSTRACT

The present invention relates to modulators of muscarinic receptors. The present invention also provides compositions comprising such modulators, and methods therewith for treating muscarinic receptor mediated diseases.

39 Claims, No Drawings

U.S. PATENT DOCUMENTS

| | | | |
|---|---|---|---|
| 2006/0019962 | A1 | 1/2006 | Makings et al. |
| 2006/0040964 | A1 | 2/2006 | Bakthavatchalam et al. |
| 2006/0058778 | A1 | 3/2006 | Baxter et al. |
| 2006/0106045 | A1 | 5/2006 | Huges et al. |
| 2006/0111380 | A1 | 5/2006 | Otake et al. |
| 2006/0173027 | A1 | 8/2006 | Marzabadi et al. |
| 2006/0183904 | A1 | 8/2006 | Guo et al. |
| 2006/0211722 | A1 | 9/2006 | Jiao et al. |
| 2006/0217372 | A1 | 9/2006 | Blanco-Pillado et al. |
| 2007/0043023 | A1 | 2/2007 | Makings et al. |
| 2007/0149502 | A1 | 6/2007 | Chaturvedula et al. |
| 2007/0254903 | A1 | 11/2007 | Boatman et al. |
| 2008/0171753 | A1 | 7/2008 | Jitsuoka et al. |

FOREIGN PATENT DOCUMENTS

| | | |
|---|---|---|
| EP | 0065864 | 12/1982 |
| EP | 0070171 | 1/1983 |
| EP | 0414289 | 2/1991 |
| EP | 0444945 | 9/1991 |
| EP | 0486280 | 5/1992 |
| GB | 1575800 | 10/1980 |
| GB | 2308064 | 6/1997 |
| JP | 59059685 | 4/1984 |
| JP | 2001/278886 | 10/2001 |
| JP | 2002/316987 | 10/2002 |
| WO | WO 94/22846 | 10/1994 |
| WO | WO 95/09631 | 4/1995 |
| WO | WO 95/11029 | 4/1995 |
| WO | WO 95/14025 | 5/1995 |
| WO | WO 95/28389 | 10/1995 |
| WO | WO 97/41878 | 11/1997 |
| WO | WO 97/41879 | 11/1997 |
| WO | WO 99/06434 | 2/1999 |
| WO | WO 99/32489 | 7/1999 |
| WO | WO 00/06146 | 2/2000 |
| WO | WO 00/06153 | 2/2000 |
| WO | WO 00/06545 | 2/2000 |
| WO | WO 00/38720 | 7/2000 |
| WO | WO 01/02386 | 1/2001 |
| WO | WO 01/22919 | 4/2001 |
| WO | WO 01/29027 | 4/2001 |
| WO | WO 01/45707 | 6/2001 |
| WO | WO 01/64213 | 9/2001 |
| WO | WO 02/094825 | 11/2002 |
| WO | WO 03/095427 | 11/2003 |
| WO | WO 2004/010942 | 2/2004 |
| WO | WO 2004/010943 | 2/2004 |
| WO | WO 2004/011427 | 2/2004 |
| WO | WO 2005/063254 | 7/2005 |
| WO | WO 2005/065779 | 7/2005 |
| WO | WO 2006/001958 | 1/2006 |
| WO | WO 2006/023852 | 3/2006 |
| WO | WO 2006/058303 | 6/2006 |

OTHER PUBLICATIONS

Bignan, G., "Preparation of 3-Spirocyclic Indolin-2-ones as Ligands for the ORL-1 Receptor", Bioorganic and Medicinal Chem. Lett, 15 (2005), pp. 5022-5026.

Butera, J., "Recent Approaches to the Treatment of Urinary Incontinence: A Survey of Patent Activity from 1995 to 1998", Expert Opinion on Therapeutic Patents, 8(8) (1998), pp. 1017-1035.

Bymaster, F., "Xanomeline: A Selective Muscarinic Agonist for the Treatment of Alzheimer's Disease", Drug Development Research, 40 (1997), pp. 158-170.

Yang, L., "Potent 3-Spiropiperidine Growth Hormone Secretagogues", Bioorganic and Medicinal Chem. Lett, 8(1) (1998), pp. 107-112.

Yang, L., "The Design and Synthesis of Non-Peptide Somatostatin Receptor Agonists", Proceedings of the American Peptide Symposium, 16th Minneapolis, MN, Jun. 26-Jul. 1, 1999, (2000), meeting date 1999, 250-252.

Chambers, M., "Spiropiperidines as High-Affinity, Selective σ Ligands", J. Med. Chem., 35(11) (1992), pp. 2033-2039.

Chiaverelli, S., "Ricerche nella serie della 4-feniipiperidina. Nota v. Derivati della 4,4'-spiro-(1"metilpiperidin)-1,2,3,4,-tetraidroisochinolina", Gazzetta Chimica Italiana, 90, 189 (1960), CN1535967.

Custers, F., "Vesamicol and Some of its Derivatives: Questionable Ligands for Selectively Labelling Acetylcholine Transporters in Rat Brain", Eur. Jour. of Pharm., 338 (1997), pp. 177-183.

deLaszlo, S., "A Nonpeptidic Agonist Ligand of the Human C5A Receptor: Synthesis, Binding Affinity Optimization and functional Characterization", Bioorganic and Medicinal Chem. Lett., 7(2) (1997), pp. 213-218.

Dhar, T.G., "Design and Synthesis of Novel α1a Adrenoceptor-Selective Antagonists. 2. Approaches to Eliminate Opioid Agonist Metabolites via Modification of Linker and 4-Methoxycarbonyl-4-phenylpiperidine Moiety1.2", J. Med. Chem, 42 (1999), pp. 4778-4793.

Efange, S., "Comparative Tissue Distribution of conformationally Restricted Radioiodinated Vesamicol Receptor Ligands", Nuclear Medicine and Biology, 22(4) (1995), pp. 437-444.

Efange, S., "Molecular Determinants of Selectivity at the Vesamicol Receptor", Biochem. Phar., 49(6) (1995), pp. 791-797.

Efange, S., "N-Hydroxyalkyl Derivatives of 3β-Phenyltropane and Methylspiro[1H-indoline-3,4'-piperidine]: Vesamicol Analogues with Affinity or Monoamine Transporters", J. Med. Chem, 40 (1997), pp. 3905-3914.

Efange, S., "(+)-p-([18F]Fluorobenzyl)Spirotrozamicol {(+)-[18F]Spiro-FBT}: Synthesis and Biological Evaluation of a High-Affinity Ligand for the Vesicular Acetylcholine Transporter (VAChT)", Nuclear Medicine and Biology, vol. 26 (1999), pp. 189-192.

Efange, S., "Spirovesamicols: Conformationally Restricted Analogs of 2-(4-Phenylpiperidino)cyclohexanol (Vesamicol, AH5183) as Potential Modulators of Presynaptic Cholinergic Function", J. Med. Chem, 37 (1994), pp. 2574-2582.

Evans, B., "Orally Active, Nonpeptide Oxytocin Antagonists", J. Med. Chem., 35(21)(1992), pp. 3919-3927.

Tata, J., "The Synthesis and Activity of Spiroindane Growth Hormone Secretagogues", Bioorganic and Medicinal Chem. Lett, 7(6) (1997), pp. 663-668.

Williams, P., "1-(((7,7-Dimethyl-2(S)-(2(S)-amino-4-(methylsulfonyl)butyramido)bicyclo[2.2.1]-heptan-1(S)-yl)methyl)sulfonyl)-4-2(2-methylphenyl)piperazine (L-368,899): An Orally Bioavailable, Non-Peptide Oxytocin Antagonist with Potential Utility for Managing Preterm Labor", J. Med. Chem, 37 (1994), pp. 555-571.

Kim, D., "Discovery of Human CCR5 Antagonists Containing Hydantoins for the Treatment of HIV-1 Infection", Bioorganic and Medicinal Chem. Lett., 11 (2001, pp. 3099-3102.

Malmstrom, R., "Pharmacology of H 394/84, a Dihydropyridine neuropeptide Y Y1 Receptor Antagonist, in Vivo", Eur. Jour. of Pharm., 418 (2001), pp. 95-104.

Matier, W., "Novel Cyclizations and Ring-Opening Reactions of 3-Phenylindene Derivatives", J. Org. Chem., vol. 36, No. 5 (1971), pp. 650-654.

Moltzen, E., "σLignads with Subnanomolar Affinity and Preference for the σ2 Binding Site. 2. Spiro-Joined Benzofuran, Isobenzofuran and Benzopyran Piperidines", J. Med. Chem., 38 (1995), pp. 2009-2017.

Morrow, D., "Synthesis of Some New 17-Spiro-Substituted Steroids", J. Med. Chem., 10(2) (1967), pp. 133-138.

Nargund, R., "Peptidomimetic Growth Hormone Secretagogues: Synthesis and Biological Activities of Analogs Varied at the Indole Nucleus of the Prototypical Spiropiperidine L-162,752", Bioorganic and Medicinal Chem. Lett., vol. 6, No. 14 (1996), pp. 1731-1736.

Nargund, R., "Synthesis and Biological Activities of Camphor-Based Non-Peptide Growth Hormone Secretagogues", Bioorganic and Medicinal Chem. Lett., vol. 6, No. 11 (1996), pp. 1265-1270.

Oprea, T., "Is There a Difference between Leads and Drugs? A Historical Perspective", J. Chem. Inf. Comput. Sci., 41 (2001), pp. 1308-1315.

Pasternak, A., "Potent, Orally Bioavailable Somatostatin Agonists: Good Absorption Achieved by Urea Backbone Cyclization", Bioorganic and Medicinal Chem. Lett., 9 (1999), pp. 491-496.

Patchett, A.A., "The Synthesis of 17β-Amino-17 α-(2'-carboxyethyl)androstane Lacatama1", J. Org. Chem, 27 (1962), pp. 3822-3828.

Pettibone, D.J., "Identification of an Orally Active, Nonpeptidyl Oxytocin Antagonist", Journal of Pharm. and Experimental Therap., 264(1) (1993), pp. 308-314.

Reimann, E., "Synthese und pharmakologische Prüfung Homologer und hydroxylierter 3,4-Dihydro-1'-methylspiro [naphthalin-(2H),4'-piperidine]", Archiv. Der. Pharmazie, VCH Verlagsgesellschaft MBH, Weinheim, DE, 323 (1990), pp. 35-39.

Takemoto, T., "Asymmetric Synthesis of Enantiomerically Pure Spiro[((2S)-hydroxy)indane-1,4'-piperidine]", Tetrahedron Asymmetry, 10 (1999), pp. 1787-1793.

Cheng, Y., "Solid Phase Synthesis of Spiroindoline", Tet. Lett., 38 (1997), pp. 1497-1500.

Maligres, P. E., "Synthesis of the Orally Active Spiroindoline-Based Growth Hormone Secretagogue, MK-677", Tetrahedron, 53 (1997), pp. 10983-10992.

Caulfield, M.P., "Muscarinic Receptors-Characterization, Coupling, and Function", Pharmacol. Ther., vol. 58 (1993), pp. 319-379.

Caufield, M.P., "International Union of Pharmacology, XVII. Classification of Muscarinic Acetylcholine Receptors", Pharmacological Reviews, vol. 50, No. 2 (1998), pp. 279-290.

DeLapp, N., "Therapeutic Opportunities for Muscarinic Receptors in the Central Nervous System", Journal of Medicinal Chemistry, vol. 43, No. 23 (2000), pp. 4333-4353.

Freireich, "Quantitative Comparison of Toxicity of Anticancer Agents in Mouse, Rat, Hamster, Dog, Monkey and Man", Cancer Chemother. Rep., 50 (1966), p. 219.

Hulme, E.C., "Muscarinic Receptor Subtypes", Annual Reviews Pharmacol. Toxicol., vol. 30, (1990), pp. 633-673.

International Search Report dated Jan. 31, 2008.

MODULATORS OF MUSCARINIC RECEPTORS

CLAIM OF PRIORITY

This application claims priority to U.S. Provisional Application Ser. No. 60/838,701 filed on Aug. 18, 2006, which is hereby incorporated by reference.

TECHNICAL FIELD OF THE INVENTION

The present invention relates to modulators of muscarinic receptors. The present invention also provides compositions comprising such modulators, and methods therewith for treating muscarinic receptor mediated diseases.

BACKGROUND OF THE INVENTION

The neurotransmitter acetylcholine binds to two types of cholinergic receptors: the ionotropic family of nicotinic receptors and the metabotropic family of muscarinic receptors. Muscarinic receptors belong to the large superfamily of plasma membrane-bound G protein coupled receptors (GPCRs). To date, five subtypes of muscarinic receptors ($M_1$-$M_5$) have been cloned and sequenced from a variety of species, and show a remarkably high degree of homology across species and receptor subtype. These $M_1$-$M_5$ muscarinic receptors are predominantly expressed within the parasympathetic nervous system which exerts excitatory and inhibitory control over the central and peripheral tissues and participate in a number of physiologic functions, including heart rate, arousal, cognition, sensory processing, and motor control.

Muscarinic agonists such as muscarine and pilocarpine, and antagonists, such as atropine have been known for over a century, but little progress has been made in the discovery of receptor subtype-selective compounds, thereby making it difficult to assign specific functions to the individual receptors. See, e.g., DeLapp, N. et al., "Therapeutic Opportunities for Muscarinic Receptors in the Central Nervous System," J. Med. Chem., 43(23), pp. 4333-4353 (2000); Hulme, E. C. et al., "Muscarinic Receptor Subtypes," Ann. Rev. Pharmacol. Toxicol., 30, pp. 633-673 (1990); Caulfield, M. P. et al., "Muscarinic Receptors-Characterization, Coupling, and Function," Pharmacol. Ther., 58, pp. 319-379 (1993); Caulfield, M. P. et al., International Union of Pharmacology. XVII. "Classification of Muscarinic Acetylcholine Receptors," Pharmacol. Rev., 50, pp. 279-290 (1998), the disclosures of which are incorporated herein by reference.

The Muscarinic family of receptors is the target of a large number of pharmacological agents used for various diseases, including leading drugs for COPD, asthma, urinary incontinence, glaucoma, Alzheimer's (AchE inhibitors). Despite the large therapeutic value of this family, cholinergic drugs are limited by the lack of selectivity of these agents, with significant activation of the parasympathetic autonomous system and elevated incidence of adverse effects. The molecular cloning of the muscarinic receptors and the identification of the physiological role of specific isoforms using knock-out mice, has recently delineated novel opportunities for selective muscarinic ligands, and has helped to define the selectivity profile that is required for enhanced efficacy and reduced side effects.

There is a need for modulators of muscarinic receptors $M_1$-$M_5$. There is also a need for methods for treating muscarinic receptor-mediated diseases.

There is also a need for modulators of muscarinic receptors that are selective as to subtypes $M_1$-$M_5$.

SUMMARY OF THE INVENTION

The present invention provides methods of modulating the activity of a muscarinic receptor (e.g., $M_1$, $M_2$, $M_3$, $M_4$, $M_5$, or combinations thereof) using compounds of formula I:

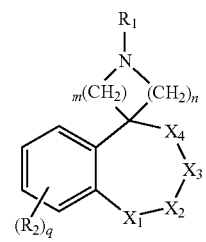

or a pharmaceutically acceptable salt thereof, wherein $R_1$, $R_2$, $X_1$, $X_2$, $X_3$, $X_4$, m, n, and q are described below.

DETAILED DESCRIPTION

I. Definitions

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "muscarinic receptor," without a prefix specifying the receptor subtype, refers to one or more of the five receptor subtypes $M_1$-$M_5$.

The term "modulating" as used herein means increasing or decreasing, e.g. activity, by a measurable amount. Compounds that modulate muscarinic activity by increasing the activity of the muscarinic receptors are called agonists. Compounds that modulate muscarinic activity by decreasing the activity of the muscarinic receptors are called antagonists. An agonist interacts with a muscarinic receptor to increase the ability of the receptor to transduce an intracellular signal in response to endogenous ligand binding. An antagonist interacts with a muscarinic receptor and competes with the endogenous ligand(s) or substrate(s) for binding site(s) on the receptor to decrease the ability of the receptor to transduce an intracellular signal in response to endogenous ligand binding.

The phrase "treating or reducing the severity of a muscarinic receptor mediated disease" refers both to treatments for diseases that are directly caused by muscarinic activities and alleviation of symptoms of diseases not directly caused by muscarinic activities. Examples of diseases whose symptoms may be affected by muscarinic activity include, but are not limited to, CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, Parkinson's disease, peripheral disorders such as reduction of intra ocular pressure in Glaucoma and treatment of dry eyes and dry mouth including Sjögren's Syndrome, bradycardia, gastric acid secretion, asthma, GI disturbances and wound healing.

As described herein, compounds of the invention may optionally be substituted with one or more substituents, such as are illustrated generally above, or as exemplified by particular classes, subclasses, and species of the invention.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-8 (e.g., 1-6 or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-SO$_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-SO$_2$-amino)alkyl), aminoalkyl, amidoalkyl, (cycloaliphatic)alkyl, or haloalkyl.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as halo, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-SO$_2$—, cycloaliphatic-SO$_2$—, or aryl-SO$_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-SO$_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-6 or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-SO$_2$—, aliphaticamino-SO$_2$—, or cycloaliphatic-SO$_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refers to an amido group such as —N(R$^X$)—C(O)—R$^Y$ or —C(O)—N(R$^X$)$_2$, when used terminally, and —C(O)—N(R$^X$)— or —N(R$^X$)—C(O)— when used internally, wherein R$^X$ and R$^Y$ are defined below. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —NR$^X$R$^Y$ wherein each of R$^X$ and R$^Y$ is independently hydrogen, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic)carbonyl, each of which being defined herein and being optionally substituted. Examples of amino groups include alkylamino, dialkylamino, or arylamino. When the term "amino" is not the terminal group (e.g., alkylcarbonylamino), it is represented by —NR$^X$—. R$^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more C$_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphatic-SO$_2$— or amino-SO$_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a C$_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a C$_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, azacycloalkyl, or ((aminocarbonyl)cycloalkyl)cycloalkyl. A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl. A cycloalkyl or cycloalkenyl group can be optionally substituted with one or more substituents such as aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-SO$_2$— and aryl-SO$_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, "cyclic moiety" includes cycloaliphatic, heterocycloaliphatic, aryl, or heteroaryl, each of which has been defined previously.

As used herein, the term "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A monocyclic heterocycloalkyl group can be fused with a phenyl moiety such as tetrahydroisoquinoline. A "heterocycloalkenyl" group, as used herein, refers to a mono- or bicyclic (e.g., 5- to 10-membered mono- or bicyclic) non-aromatic ring structure having one or more double bonds, and wherein one or more of the ring atoms is a heteroatom (e.g., N, O, or S). Monocyclic and bicycloheteroaliphatics are numbered according to standard chemical nomenclature.

A heterocycloalkyl or heterocycloalkenyl group can be optionally substituted with one or more substituents such as aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic)carbonylamino, (aryl)carbonylamino, (araliphatic)carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic) carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b] thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1, 2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic) oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic) carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl) amino)heteroaryl]; (cyanoalkyl)heteroaryl; (alkoxy)heteroaryl; (sulfamoyl)heteroaryl [e.g., (aminosulfonyl) heteroaryl]; (sulfonyl)heteroaryl [e.g., (alkylsulfonyl) heteroaryl]; (hydroxyalkyl)heteroaryl; (alkoxyalkyl) heteroaryl; (hydroxy)heteroaryl; ((carboxy)alkyl)heteroaryl; (((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl, and (haloalkyl)heteroaryl [e.g., trihaloalkylheteroaryl].

A "heteroaraliphatic (such as a heteroalkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$ or —NR$^X$—CO— O—R$^Z$ wherein R$^X$ and R$^Y$ have been defined above and R$^Z$ can be aliphatic, aryl, araliphatic, heterocycloaliphatic, heteroaryl, or heteroaraliphatic.

As used herein, a "carboxy" group refers to —COOH, —COOR$^X$, —OC(O)H, —OC(O)R$^X$ when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —CF$_3$.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfonamide" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)— when used internally, wherein R$^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$— when used internally, wherein R$^X$ has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic(amido(aliphatic)))-S(O)$_2$— or the like.

As used herein, a "sulfoxy" group refers to —O—SO—R$^X$ or —SO—O—R$^X$, when used terminally and —O—S(O)— or —S(O)—O— when used internally, where R$^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, an "aminoalkyl" refers to the structure (R$^X$)$_2$N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ have been defined above.

As used herein, a "guanidine" group refers to the structure —N=C(N(R$^X$R$^Y$))N(R$^X$R$^Y$) or —NR$^X$—C(=NR$^X$)NR$^X$R$^Y$ wherein R$^X$ and R$^Y$ have been defined above.

As used herein, the term "amidino" group refers to the structure —C=(NR$^X$)N(R$^X$R$^Y$) wherein R$^X$ and R$^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R$^X$O(O)C-alkyl is an example of a carboxy group used terminally. A group is internal when the group is present in the middle of a substituent to at the end of the substituent bound to the rest of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, "cyclic group" includes mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxabicyclo[2.2.2]octyl, 1-azabicyclo[2.2.2]octyl, 3-azabicyclo[3.2.1]octyl, and 2,6-dioxa-tricyclo[3.3.1.0$^{3,7}$]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "aliphatic chain" refers to a branched or straight aliphatic group (e.g., alkyl groups, alkenyl groups, or alkynyl groups). A straight aliphatic chain has the structure —[CH$_2$]$_v$—, where v is 1-6. A branched aliphatic chain is a straight aliphatic chain that is substituted with one or more aliphatic groups. A branched aliphatic chain has the structure —[CHQ]$_v$- or —[CQQ]$_v$- where Q is hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables in formulae (I, I-A, and I-B), e.g., R$_1$, R$_2$, X$_1$, X$_2$, X$_3$, and X$_4$, and other variables contained therein encompass specific groups, such as alkyl and aryl. Unless otherwise noted, each of the specific groups for the variables $R_1$, $R_2$, $X_1$, $X_2$, $X_3$, and $X_4$, and other variables contained therein can be optionally substituted with one or more substituents described herein. Each substituent of a specific group is further optionally substituted with one to three of halo, cyano, oxo, alkoxy, hydroxy, amino, nitro, aryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an effective amount is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, (Z) and (E) conformational isomers, and tautomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

II. Methods

A. Generic Description

The present invention provides methods of modulating the activity of a muscarinic receptor comprising the step of contacting said receptor with a compound of formula I:

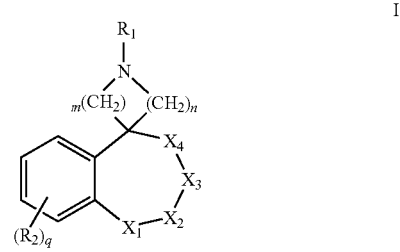

I a pharmaceutically acceptable salt thereof, wherein $X_1$ is $-NR_{3A}-$;

$X_2$ is $-CR'_{3B}R'_{3C}-$;

$X_3$ is $-CR_{4A}R_{4B}-$;

$X_4$ is $-CR'_{4C}R'_{4B}-$;

$R_1$ is hydrogen, optionally substituted $C_{1-12}$ aliphatic, optionally substituted cycloaliphatic, or optionally substituted heterocycloaliphatic;

Each $R_2$ is independently $-Z^A R_5$, wherein each $Z^A$ is independently a bond or is an optionally substituted $C_{1-8}$ aliphatic chain wherein up to two carbon units of $Z^A$ are optionally and independently replaced by $-CO-$, $-CS-$, $-COCO-$, $-CONR^A-$, $-CONR^A NR^A-$, $-CO_2-$, $-OCO-$, $-NR^A CO_2-$, $-O-$, $-NR^A CONR^A-$, $-OCONR^A-$, $-NR^A NR^A-$, $-NR^A NR^A CO-$, $-NR^A CO-$, $-S-$, $-SO-$, $-SO_2-$, $-NR^A-$, $-SO_2 NR^A-$, $-NR^A SO_2-$, $-P(O)(OR^A)-$, $-P(O)(OR^A)NR^A-$ or $-NR^A SO_2 NR^A-$, Each $R_5$ is independently $R^A$, halo, $-OH$, $-NH_2$, $-NO_2$, $-CN$, $-CF_3$, or $-OCF_3$, Each $R^A$ is independently hydrogen, optionally substituted $C_{1-6}$ aliphatic, optionally substituted cycloaliphatic, optionally substituted heterocycloaliphatic, optionally substituted aryl, or optionally substituted heteroaryl, or $R_2$ and $R_{3A}$ together with the atoms to which they are attached form an optionally substituted 4-10 membered heterocyclic or carbocyclic ring, Each of $R_{3A}$, $R'_{3B}$, and $R'_{3C}$ is independently $-Z^B R_6$, wherein each $Z^B$ is independently a bond or is an optionally substituted $C_{1-8}$ aliphatic chain wherein up to two carbon units of $Z^B$ are optionally and independently replaced by $-CO-$, $-CS-$, $-COCO-$, $-CONR^B-$, $-CONR^B NR^B-$, $-CO_2-$, $-OCO-$, $-NR^B CO_2-$, $-O-$, $-NR^B CONR^B-$, $-OCONR^B-$, $-NR^B NR^B-$, $-NR^B NR^B CO-$, $-NR^B CO-$, $-S-$, $-SO-$, $-SO_2-$, $-NR^B-$, $-SO_2 NR^B-$, $-NR^B SO_2-$, $-P(O)(OR^B)$, $-P(O)(ORB)NR^B-$ or $-NR^B SO_2 NR^B-$, Each $R_6$ is independently $R^B$, halo, $-OH$, $-NH_2$, $-NO_2$, $-CN$, $-CF_3$, or $-OCF_3$, Each $R^B$ is independently hydrogen, optionally substituted $C_{1-6}$ aliphatic, optionally substituted cycloaliphatic, optionally substituted heterocycloaliphatic, optionally substituted aryl, or optionally substituted heteroaryl, or R'$_{3B}$ and R'$_{3C}$ together with the carbon atom to which they are attached form a carbonyl group, or One of R$_{3A}$ or R'$_{3B}$ and R$_{4A}$ together with the atoms to which they are attached form an optionally substituted 3-10 membered cycloaliphatic or an optionally substituted 3-10 membered heterocycloaliphatic;

Each of R$_{4A}$, R'$_{4A}$, R$_{4B}$, and R'$_{4B}$ is independently —Z$^C$R$_7$, wherein each Z$^C$ is independently a bond or is an optionally substituted C$_{1-8}$ aliphatic chain wherein up to two carbon units of Z$^C$ are optionally and independently replaced by —CO—, —CS—, —COCO—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —NR$^C$NR$^C$—, —NR$^C$NR$^C$CO—, —NR$^C$CO—, —S—, —SO, —SO$_2$—, —NR$^C$—, —SO$_2$NR$^C$—, —NR$^C$SO$_2$—, —P(O)(OR$^C$)—, —P(O)(OR$^C$)NR$^C$— or —NR$^C$SO$_2$NR$^C$—, Each R$_7$ is independently R$^C$, halo, —OH, —NH$_2$, —NO$_2$, —CN, —CF$_3$, or —OCF$_3$, Each R$^C$ is independently hydrogen, optionally substituted C$_{1-6}$ aliphatic, optionally substituted cycloaliphatic, optionally substituted heterocycloaliphatic, optionally substituted aryl, or optionally substituted heteroaryl, or R$_{4A}$ and R$_{4B}$ together with the carbon atom to which they are attached form a carbonyl group;

m is 1-3;

n is 1-3; and q is 0-4.

B. Specific Description

1. Substituent R$_1$

R$_1$ is hydrogen, optionally substituted C$_{1-12}$ aliphatic, optionally substituted cycloaliphatic, or optionally substituted heterocycloaliphatic.

In some embodiments, R$_1$ is —Z$^D$R$_8$, wherein each Z$^D$ is independently a bond or an optionally substituted branched or straight C$_{1-12}$ aliphatic chain wherein up to two carbon units of Z$^D$ are optionally and independently replaced by —CO—, —CS—, —CONR$^D$—, —CONR$^D$NR$^D$, —CO$_2$—, —OCO—, —NR$^D$CO$_2$—, —O—, —NR$^D$CONR$^D$—, —OCONR$^D$—, —NR$^D$NR$^D$—, —NR$^D$CO—, —S—, —SO—, —SO$_2$—, —NR$^D$—, —SO$_2$NR$^D$—, —NR$^D$SO$_2$—, or —NR$^D$SO$_2$NR$^D$—. Each R$_8$ is independently R$^D$, halo, —OH, —NH$_2$, —NO$_2$, —CN, or —OCF$_3$. Each R$^D$ is independently hydrogen or an optionally substituted aliphatic, an optionally substituted cycloaliphatic, or an optionally substituted heterocycloaliphatic.

In some embodiments, R$_1$ is an optionally substituted C$_{1-12}$ aliphatic. In another embodiments, R$_1$ is an optionally substituted group selected from C$_{1-12}$ alkyl, C$_{1-12}$ alkenyl, or C$_{1-12}$ alkynyl. In yet another embodiment, R$_1$ is an optionally substituted C$_{1-6}$ alkyl. In several examples, R$_1$ is selected from methyl, ethyl, n-propyl, isopropyl, n-butyl, sec-butyl, t-butyl, hexyl, 3,3-dimethylbutyl, or 3-methylbutyl, each of which is optionally substituted with a cycloaliphatic, a heterocycloaliphatic, an alkylsulfanyl, an alkoxy, an amino, or combinations thereof, where each of which is optionally substituted.

In some embodiments, R$_1$ is an optionally substituted cycloaliphatic. In several examples, R$_1$ is an optionally substituted group selected from a monocyclic cycloaliphatic or a bicyclic cycloaliphatic. In another example, R$_1$ is an optionally substituted group selected from cyclopropyl, cyclobutyl, cyclopentyl, cyclohexyl, cycloheptyl, or cyclooctyl, each of which is optionally substituted with 1-3 of halo, aliphatic, hydroxy, alkoxycarbonyl, cycloaliphatic, or combinations thereof.

In some embodiments, R$_1$ is an optionally substituted 7-10 membered bicyclic cycloaliphatic. In several examples, R$_1$ is an optionally substituted group selected from 7-10 membered bicyclic cycloalkyl or 7-10 membered bicyclic cycloalkenyl. In another examples, R$_1$ is an optionally substituted group selected from bicyclo[2.1.1]hexane-yl, bicyclo[2.2.1]heptane-yl, bicyclo[2.2.2]octane, bicyclo[3.1.1]heptane, bicyclo[3.2.1]octane-yl, or bicyclo[3.3.1]nonane-yl, bicyclo[2.1.1]hex-2-ene-yl, bicyclo[2.2.1]hept-2-ene-yl, bicyclo[2.2.2]oct-2-ene-yl, each of which is optionally substituted with 1-3 of halo, aliphatic, hydroxy, amino, acyl, or combinations thereof.

In some embodiments, R$_1$ is an optionally substituted group selected from monocyclic heterocycloaliphatic or a bicyclic heterocycloaliphatic. In some examples, R$_1$ is an optionally substituted 3-8 membered monocyclic cycloaliphatic having 1-3 heteroatoms selected from N, O, and S. In another examples, R$_1$ is a tetrahydrofuran-yl, tetrahydro-2H-thiopyran-yl, pyrrolidine-yl, imidazolidine-yl, 1,4-dioxane-yl, morpholine-yl, piperidine-yl, piperazine-yl, tetrahydro-2H-pyran-yl, pyrazolidine-yl, or thiomorpholine-yl, each of which is optionally substituted with 1-3 of halo, amido, acyl, (heterocycloaliphatic)carbonyl, alkenyloxycarbonyl or combinations thereof.

In some embodiments, R$_1$ is an optionally substituted 7-10 membered bicyclic heterocycloaliphatic having 1-2 heteroatoms selected from N, O, and S. In several examples, R$_1$ is an optionally substituted 7-10 membered bridged bicyclic heterocycloaliphatic or an optionally substituted 7-10 membered fused bicyclic heterocycloaliphatic. In another examples, R$_1$ is 8-azabicyclo[3.2.1]octane-yl, or azabicyclo[2.2.1]heptane-yl, each of which is optionally substituted with 1-3 of halo, aliphatic, hydroxy, amino, acyl, or combinations thereof.

In several alternative embodiments, R$_1$ is one selected from: hydrogen; cyclohexylmethyl; 3,3-dimethylbutyl; bicyclo[2.2.1]hept-5-en-2-yl; cyclohept-1-yl; bicyclo[2.2.1]heptane-2-yl; 1-ethoxycarbonylpiperidine-4-yl; 8-ethoxycarbonyl-8-azabicyclo[3.2.1]octane-3-yl; 3-methylbutyl; (tetrahydro-2H-pyran-4-yl)ethyl; 4-(methyl(sulfanyl))butyl; 3,7-dimethyl-7-methoxyoctyl; (tetrahydro-2H-thiopyran-4-yl)ethyl; cyclohexyl; cycloheptyl; cyclopentyl; (N,N-dimethylaminocarbonyl)piperidine-4-yl; N-acetylpiperidine-4-yl; 1-(cyclopropyl(carbonyl))piperidine-4-yl; (prop-2-ynoxy(carbonyl))piperidine-4-yl; piperidine-4-yl; propoxycarbonylpiperidine-4-yl; (prop-2-enoxy(carbonyl))piperidine-4-yl; (morpholine-4-yl(carbonyl))piperidine-4-yl; and 1-methoxycarbonylpiperidine-4-yl; bicyclo[2.2.1]hept-5-en-2-ylmethyl; and isopropylcarbonylpiperidine-4-yl.

2. X$_1$, X$_2$, X$_3$, and X$_4$ Groups

X$_1$ is —NR$_{3A}$—, and X$_2$ is —CR'$_{3B}$R'$_{3C}$—; wherein each of R$_{3A}$, R'$_{3B}$, and R'$_{3C}$ is independently —Z$^B$R$_6$, wherein each Z$^B$ is independently a bond or is an optionally substituted C$_{1-8}$ aliphatic chain wherein up to two carbon units of Z$^B$ are optionally and independently replaced by —CO—, —CS—, —COCO—, —CONR$^B$—, —CONR$^B$NR$^B$—, —CO$_2$—, —OCO—, —NR$^B$CO$_2$—, —O—, —NR$^B$CONR$^B$—, —OCONR$^B$—, —NR$^B$NR$^B$, —NR$^B$NR$^B$CO—, —NR$^B$CO—, —S—, —SO—, —SO$_2$—, —NR$^B$—, —SO$_2$NR$^B$—, —NR$^B$SO$_2$—, —P(O)(OR$^B$)—, —P(O)(OR$^B$)NR$^B$— or —NR$^B$SO$_2$NR$^B$—; each R$_6$ is independently R$^B$, halo, —OH, —NH$_2$, —NO$_2$, —CN, —CF$_3$, or —OCF$_3$; and each R$^B$ is independently hydrogen, optionally substituted C$_{1-6}$ aliphatic, optionally substituted cycloaliphatic, optionally substituted heterocycloaliphatic, optionally substituted aryl, or optionally substituted heteroaryl. Alternatively, R'$_{3B}$ and R'$_{3C}$ together with the carbon atom to which they are attached form a carbonyl group, or one of $R_{3A}$ or $R'_{3B}$ and $R_{4A}$ together with the atoms to which they are attached form an optionally substituted 3-10 membered cycloaliphatic ring or an optionally substituted 3-10 membered heterocycloaliphatic ring.

$X_3$ is —$CR_{4A}R_{4B}$—, and $X_4$ is —$CR'_{4C}R'_{4B}$—; wherein each of $R_{4A}$, $R'_{4A}$, $R_{4B}$, and $R'_{4B}$ is independently —$Z^C R_7$, wherein each $Z^C$ is independently a bond or is an optionally substituted $C_{1-8}$ aliphatic chain wherein up to two carbon units of $Z^C$ are optionally and independently replaced by —CO—, —CS—, —COCO—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —NR$^C$NR$^C$—, —NR$^C$NR$^C$CO—, —NR$^C$CO—, —S—, —SO, —SO$_2$—, —NR$^C$—, —SO$_2$NR$^C$—, —NR$^C$SO$_2$—, —P(O)(OR$^C$)—, —P(O)(OR$^C$)NR$^C$— or —NR$^C$SO$_2$NR$^C$—; each $R_7$ is independently R$^C$, halo, —OH, —NH$_2$, —NO$_2$, —CN, —CF$_3$, or —OCF$_3$; and each R$^C$ is independently hydrogen, optionally substituted $C_{1-6}$ aliphatic, optionally substituted cycloaliphatic, optionally substituted heterocycloaliphatic, optionally substituted aryl, or optionally substituted heteroaryl. Alternatively, $R_{4A}$ and $R_{4B}$ together with the carbon atom to which they are attached form a carbonyl group.

In some embodiments, $X_1$ is —$NR_{3A}$— and $X_2$ is —$CR'_{3A}R'_{3B}$—. For example, $X_1$ is —$NR_{3A}$— and $X_2$ is —$CR'_{3B}R'_{3C}$—, wherein $R_{3B}$ and $R_{3C}$ together with the carbon atom to which they are attached form a carbonyl group. In another example, $X_1$ is —$NR_{3A}$— and $X_2$ is —$CR'_{3B}R'_{3C}$—, wherein each of $R'_{3B}$ and $R'_{3C}$ is hydrogen.

In several embodiments, $X_1$ is —$NR_{3A}$—, wherein $R_{3A}$ is —$Z^B R_6$, each $Z^B$ is independently a bond, or an independently and optionally substituted branched or straight $C_{1-6}$ aliphatic chain wherein up to two carbon units of $Z$ are optionally and independently replaced by —CO—, —CONR$^B$—, —CO$_2$—, —NR$^B$CO$_2$—, —SO$_2$—, —O—, or —NR$^B$CO—, $R_6$ is R$^B$, and each R$^B$ is hydrogen or optionally substituted $C_{1-3}$ aliphatic. For example, $X_1$ is —$NR_{3A}$—, wherein $R_{3A}$ is —$Z^B R_6$, each $Z^B$ is —CO—, —CONH—, —CO$_2$—, —NHCO$_2$—, —SO$_2$—, —O—, or —NHCO—, and $R_6$ is hydrogen or optionally substituted $C_{1-3}$ aliphatic. In other examples, $X_1$ is —$NR_{3A}$—, wherein $R_{3A}$ is $Z^B R_6$, $Z^B$ is —CO— or —CONH—, and $R_6$ is hydrogen or optionally substituted $C_{1-3}$ aliphatic.

In several embodiments, $X_2$ is —$CR'_{3B}R'_{3C}$—, wherein $R'_{3B}$ and $R'_{3C}$ are each hydrogen, or $R'_{3B}$ and $R'_{3C}$ together with the carbon atom to which they are attached form a carbonyl group.

In other embodiments, $X_1$ is —$NR_{3A}$—, wherein $R_{3A}$ is one selected from hydrogen, aminocarbonyl, methyl, methylcarbonyl, and N,N-dimethylaminocarbonyl; and $X_2$ is —$CR'_{3B}R'_{3C}$—, wherein each of $R'_{3B}$ and $R'_{3C}$ are hydrogen or $R'_{3B}$ and $R'_{3C}$ together with the carbon atom to which they are attached form a carbonyl group.

In other embodiments, $X_3$ is —$CR_{4A}R_{4B}$—, wherein $R_{4A}$ and $R_{4B}$ together with the carbon atom to which they are attached form a carbonyl group, or each of $R_{4A}$ and $R_{4B}$ is hydrogen.

In several embodiments, $X_4$ is —$CR'_{4A}R'_{4B}$—, wherein each of $R'_{4A}$ and $R'_{4B}$ are hydrogen.

3. $R_2$ Group

Each $R_2$ is independently —$Z^A R_5$, wherein each $Z^A$ is independently a bond or is an optionally substituted $C_{1-8}$ aliphatic chain wherein up to two carbon units of $Z^A$ are optionally and independently replaced by —CO—, —CS—, —COCO—, —CONR$^A$—, —CONR$^A$NR$^A$—, —CO$_2$—, —OCO—, —NR$^A$CO$_2$—, —O—, —NR$^A$CONR$^A$—, —OCONR$^A$—, —NR$^A$NR$^A$—, —NR$^A$NR$^A$CO—, —NR$^A$CO—, —S—, —SO—, —SO$_2$—, —NR$^A$—, —SO$_2$NR$^A$—, —NR$^A$SO$_2$—, —P(O)(OR$^A$)—, —P(O)(OR$^A$)NR$^A$— or —NR$^A$SO$_2$NR$^A$—; each $R_5$ is independently R$^A$, halo, —OH, —NH$_2$, —NO$_2$, —CN, —CF$_3$, or —OCF$_3$; and each R$^A$ is independently hydrogen, optionally substituted $C_{1-6}$ aliphatic, optionally substituted cycloaliphatic, optionally substituted heterocycloaliphatic, optionally substituted aryl, or optionally substituted heteroaryl. Alternatively, $R_2$ and one of $R_{3A}$ or $R_{3B}$ together with the atoms to which they are attached form an optionally substituted 4-10 membered heterocyclic or carbocyclic ring.

In several embodiments, each $R_2$ is hydrogen or optionally substituted $C_{1-6}$ aliphatic. For example, $R_2$ is an optionally substituted methyl, ethyl, propyl, butyl, ethenyl, propenyl, butenyl, or combinations thereof, each of which is optionally substituted.

In other embodiments, each $R_2$ is hydrogen.

4. m, n, and q groups m is 1-3.

n is 1-3.

q is 0-4.

In several embodiments, m is 1, 2, or 3.

In other embodiments, n is 1, 2, or 3. For example, m+n is 4. In another example, m and n are 2.

In some embodiments, q is 0, 1, 2, 3, or 4. For example, q is 0 or 4.

C. Subgeneric Methods

Another aspect of the present invention provides methods of modulating the activity of a muscarinic receptor comprising the step of contacting said receptor with a compound of formula I-A:

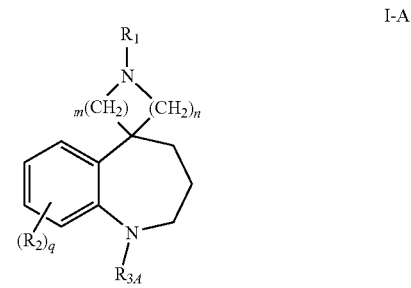

I-A or a pharmaceutically acceptable salt thereof, wherein $R_1$, $R_2$, $R_{3A}$, m, n, and q are define above in formula I.

Another aspect of the present invention provides methods of modulating the activity of a muscarinic receptor comprising the step of contacting said receptor with a compound of formula I-B:

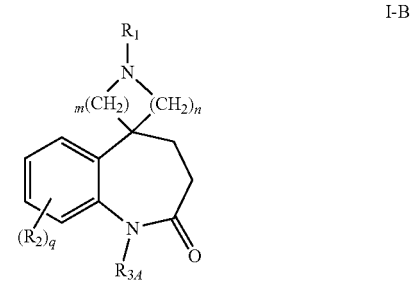

I-B or a pharmaceutically acceptable salt thereof, wherein $R_1$, $R_2$, $R_{3A}$, m, n, and q are define above in formula I.

III. Compounds

A. Generic Description

The present invention provides a compound of formula I:

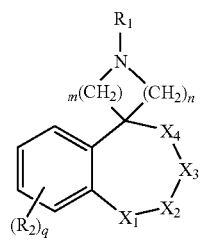

a pharmaceutically acceptable salt thereof, wherein
$X_1$ is —$NR_{3A}$—;
$X_2$ is —$CR'_{3B}R'_{3C}$—;
$X_3$ is —$CR_{4A}R_{4B}$—;
$X_4$ is —$CR'_{4C}R'_{4B}$—;
$R_1$ is hydrogen, optionally substituted $C_{1-12}$ aliphatic, optionally substituted cycloaliphatic, or optionally substituted heterocycloaliphatic;

Each $R_2$ is independently $Z^A R_5$, wherein each $Z^A$ is independently a bond or is an optionally substituted $C_{1-8}$ aliphatic chain wherein up to two carbon units of $Z^A$ are optionally and independently replaced by —CO—, —CS—, —COCO—, —$CONR^A$, —$CONR^A NR^A$—, —$CO_2$—, —OCO—, —$NR^A CO_2$—, —O—, —$NR^A CONR^A$—, —$OCONR^A$—, —$NR^A NR^A$—, —$NR^A NR^A CO$—, —$NR^A CO$—, —S—, —SO—, —$SO_2$—, —$NR^A$—, —$SO_2 NR^A$—, —$NR^A SO_2$—, —P(O)($OR^A$)—, —P(O)($OR^A$)$NR^A$— or —$NR^A SO_2 NR^A$, Each $R_5$ is independently $R^A$, halo, —OH, —$NH_2$, —$NO_2$, —CN, —$CF_3$, or —$OCF_3$, Each $R^A$ is independently hydrogen, optionally substituted $C_{1-6}$ aliphatic, optionally substituted cycloaliphatic, optionally substituted heterocycloaliphatic, optionally substituted aryl, or optionally substituted heteroaryl, or $R_2$ and $R_{3A}$ together with the atoms to which they are attached form an optionally substituted 4-10 membered heterocyclic or carbocyclic ring, Each of $R_{3A}$, $R'_{3B}$, and $R'_{3C}$ is independently —$Z^B R_6$, wherein each $Z^B$ is independently a bond or is an optionally substituted $C_{1-8}$ aliphatic chain wherein up to two carbon units of $Z^B$ are optionally and independently replaced by —CO—, —CS—, —COCO—, —$CONR^B$—, —$CONR^B NR^B$—, —$CO_2$—, —OCO—, —$NR^B CO_2$—, —O—, —$NR^B CONR^B$—, —$OCONR^B$—, —$NR^B NR^B$—, —$NR^B NR^B CO$—, —$NR^B CO$—, —S—, —SO—, —$SO_2$—, —$NR^B$—, —$SO_2 NR^B$—, —$NR^B SO_2$—, —P(O)($OR^B$)—, —P(O)($OR^B$)$NR^B$— or —$NR^B SO_2 NR^B$—, Each $R_6$ is independently $R^B$, halo, —OH, —$NH_2$, —$NO_2$, —CN, —$CF_3$, or —$OCF_3$, Each $R^B$ is independently hydrogen, optionally substituted $C_{1-6}$ aliphatic, optionally substituted cycloaliphatic, optionally substituted heterocycloaliphatic, optionally substituted aryl, or optionally substituted heteroaryl, or $R'_{3B}$ and $R'_{3C}$ together with the carbon atom to which they are attached form a carbonyl group, or One of $R_{3A}$ or $R'_{3B}$ and $R_{4A}$ together with the atoms to which they are attached form an optionally substituted 3-10 membered cycloaliphatic or an optionally substituted 3-10 membered heterocycloaliphatic;

Each of $R_{4A}$, $R'_{4A}$, $R_{4B}$, and $R'_{4B}$ is independently —$Z^C R_7$, wherein each $Z^C$ is independently a bond or is an optionally substituted $C_{1-8}$ aliphatic chain wherein up to two carbon units of $Z^C$ are optionally and independently replaced by —CO—, —CS—, —COCO—, —$CONR^C$—, —$CONR^C NR^C$—, —$CO_2$—, —OCO—, —$NR^C CO_2$—, —O—, —$NR^C CONR^C$—, —$OCONR^C$—, —$NR^C NR^C$—, —$NR^C NR^C CO$—, —$NR^C CO$—, —S—, —SO—, —$SO_2$—, —$NR^C$—, —$SO_2 NR^C$—, —$NR^C SO_2$—, —P(O)($OR^C$)—, —P(O)($OR^C$)$NR^C$— or —$NR^C SO_2 NR^C$—, Each $R_7$ is independently $R^C$, halo, —OH, —$NH_2$, —$NO_2$, —CN, —$CF_3$, or —$OCF_3$, Each $R^C$ is independently hydrogen, optionally substituted $C_{1-6}$ aliphatic, optionally substituted cycloaliphatic, optionally substituted heterocycloaliphatic, optionally substituted aryl, or optionally substituted heteroaryl, or $R_{4A}$ and $R_{4B}$ together with the carbon atom to which they are attached form a carbonyl group;

m is 1-3;
n is 1-3; and
q is 0-4.

B. Specific Description

1. Substituent $R_1$ $R_1$ is hydrogen, optionally substituted $C_{1-12}$ aliphatic, optionally substituted cycloaliphatic, or optionally substituted heterocycloaliphatic.

In some embodiments, $R_1$ is —$Z^D R_8$, wherein each $Z^D$ is independently a bond or an optionally substituted branched or straight $C_{1-12}$ aliphatic chain wherein up to two carbon units of $Z^D$ are optionally and independently replaced by —CO—, —CS—, —$CONR^D$—, —$CONR^D NR^D N^D$—, —$CO_2$—, —OCO—, —$NR^D CO_2$—, —O—, —$NR^D CONR^D$—, —$OCONR^D$—, —$NR^D NR^D$—, —$NR^D CO$—, —S—, —SO—, —$SO_2$—, —$NR^D$—, —$SO_2 NR^D$—, —$NR^D SO_2$—, or —$NR^D SO_2 NR^D$—. Each $R_8$ is independently $R^D$, halo, —OH, —$NH_2$, —$NO_2$, —CN, or —$OCF_3$. Each $R^D$ is independently hydrogen or an optionally substituted aliphatic, an optionally substituted cycloaliphatic, or an optionally substituted heterocycloaliphatic.

In some embodiments, $R_1$ is an optionally substituted $C_{1-12}$ aliphatic. In another embodiment, $R_1$ is an optionally substituted group selected from $C_{1-12}$ alkyl, $C_{1-12}$ alkenyl, or $C_{1-12}$ alkynyl. In yet another embodiment, $R_1$ is an optionally substituted $C_{1-6}$ alkyl. In several examples, $R_1$ is selected from methyl, ethyl, n-propyl, isopropyl, n-butyl, sec-butyl, t-butyl, hexyl, 3,3-dimethylbutyl, or 3-methylbutyl, each of which is optionally substituted with a cycloaliphatic, a heterocycloaliphatic, an alkylsulfanyl, an alkoxy, an amino, or combinations thereof, where each of which is optionally substituted.

In some embodiments, $R_1$ is an optionally substituted cycloaliphatic. In several examples, $R_1$ is an optionally substituted group selected from a monocyclic cycloaliphatic or a bicyclic cycloaliphatic. In another example, $R_1$ is an optionally substituted group selected from cyclopropyl, cyclobutyl, cyclopentyl, cyclohexyl, cycloheptyl, or cyclooctyl, each of which is optionally substituted with 1-3 of halo, aliphatic, hydroxy, alkoxycarbonyl, cycloaliphatic, or combinations thereof.

In some embodiments, $R_1$ is an optionally substituted 7-10 membered bicyclic cycloaliphatic. In several examples, $R_1$ is an optionally substituted group selected from 7-10 membered bicyclic cycloalkyl or 7-10 membered bicyclic cycloalkenyl. In another examples, $R_1$ is an optionally substituted group selected from bicyclo[2.1.1]hexane-yl, bicyclo[2.2.1]heptane-yl, bicyclo[2.2.2]octane, bicyclo[3.1.1]heptane, bicyclo[3.2.1]octane-yl, or bicyclo[3.3.1]nonane-yl, bicyclo[2.1.1]hex-2-ene-yl, bicyclo[2.2.1]hept-2-ene-yl, bicyclo[2.2.2]oct-2-ene-yl, each of which is optionally substituted with 1-3 of halo, aliphatic, hydroxy, amino, acyl, or combinations thereof.

In some embodiments, $R_1$ is an optionally substituted group selected from monocyclic heterocycloaliphatic or a bicyclic heterocycloaliphatic. In some examples, $R_1$ is an optionally substituted 3-8 membered monocyclic cycloaliphatic having 1-3 heteroatoms selected from N, O, and S. In another examples, $R_1$ is a tetrahydrofuran-yl, tetrahydro-2H-thiopyran-yl, pyrrolidine-yl, imidazolidine-yl, 1,4-dioxane-yl, morpholine-yl, piperidine-yl, piperazine-yl, tetrahydro-2H-pyran-yl, pyrazolidine-yl, or thiomorpholine-yl, each of which is optionally substituted with 1-3 of halo, amido, acyl, (heterocycloaliphatic)carbonyl, alkenyloxycarbonyl or combinations thereof.

In some embodiments, $R_1$ is an optionally substituted 7-10 membered bicyclic heterocycloaliphatic having 1-2 heteroatoms selected from N, O, and S. In several examples, $R_1$ is an optionally substituted 7-10 membered bridged bicyclic heterocycloaliphatic or an optionally substituted 7-10 membered fused bicyclic heterocycloaliphatic. In another examples, $R_1$ is 8-azabicyclo[3.2.1]octane-yl, or azabicyclo[2.2.1]heptane-yl, each of which is optionally substituted with 1-3 of halo, aliphatic, hydroxy, amino, acyl, or combinations thereof.

In several alternative embodiments, $R_1$ is one selected from: hydrogen; cyclohexylmethyl; 3,3-dimethylbutyl; bicyclo[2.2.1]hept-5-en-2-yl; cyclohept-1-yl; bicyclo[2.2.1]heptane-2-yl; 1-ethoxycarbonylpiperidine-4-yl; 8-ethoxycarbonyl-8-azabicyclo[3.2.1]octane-3-yl; 3-methylbutyl; (tetrahydro-2H-pyran-4-yl)ethyl; 4-(methyl(sulfanyl))butyl; 3,7-dimethyl-7-methoxyoctyl; (tetrahydro-2H-thiopyran-4-yl)ethyl; cyclohexyl; cycloheptyl; cyclopentyl; (N,N-dimethylaminocarbonyl)piperidine-4-yl; N-acetylpiperidine-4-yl; 1-(cyclopropyl(carbonyl))piperidine-4-yl; (prop-2-ynoxy(carbonyl))piperidine-4-yl; piperidine-4-yl; propoxycarbonylpiperidine-4-yl; (prop-2-enoxy(carbonyl))piperidine-4-yl; (morpholine-4-yl(carbonyl))piperidine-4-yl; and 1-methoxycarbonylpiperidine-4-yl; bicyclo[2.2.1]hept-5-en-2-ylmethyl; and isopropylcarbonylpiperidine-4-yl.

2. $X_1$, $X_2$, $X_3$, and $X_4$ Groups $X_1$ is $-NR_{3A}-$, and $X_2$ is $-CR'_{3B}R'_{3C}-$; wherein each of $R_{3A}$, $R'_{3B}$, and $R'_{3C}$ is independently $-Z^B R_6$, wherein each $Z^B$ is independently a bond or is an optionally substituted $C_{1-8}$ aliphatic chain wherein up to two carbon units of $Z^B$ are optionally and independently replaced by $-CO-$, $-CS-$, $-COCO-$, $-CONR^B-$, $-CONR^B NR^B-$, $-CO_2-$, $-OCO-$, $-NR^B CO_2-$, $-O-$, $-NR^B CONR^B-$, $-OCONR^B-$, $-NR^B NR^B-$, $-NR^B NR^B CO-$, $-NR^B CO-$, $-S-$, $-SO-$, $-SO_2-$, $-NR^B-$, $-SO_2 NR^B-$, $-NR^B SO_2-$, $-P(O)(OR^B)-$, $-P(O)(ORB)NR^B-$ or $-NR^B SO_2 NR^B-$; each $R_5$ is independently $R^B$, halo, $-OH$, $-NH_2$, $-NO_2$, $-CN$, $-CF_3$, or $-OCF_3$; and each $R^B$ is independently hydrogen, optionally substituted $C_{1-6}$ aliphatic, optionally substituted cycloaliphatic, optionally substituted heterocycloaliphatic, optionally substituted aryl, or optionally substituted heteroaryl. Alternatively, $R_2$ and $R_{3A}$ together with the atoms to which they are attached form an optionally substituted 4-10 membered heterocyclic, or $R'_{3B}$ and $R'_{3C}$ together with the carbon atom to which they are attached form a carbonyl group, or one of $R_{3A}$ or $R'_{3B}$ and $R_{4A}$ together with the atoms to which they are attached form an optionally substituted 3-10 membered cycloaliphatic ring or an optionally substituted 3-10 membered heterocycloaliphatic ring.

$X_3$ is $-CR_{4A}R_{4B}-$, and $X_4$ is $-CR'_{4C}R'_{4B}-$; wherein each of $R_{4A}$, $R'_{4A}$, $R_{4B}$, and $R'_{4B}$ is independently $-Z^C R_7$, wherein each $Z^C$ is independently a bond or is an optionally substituted $C_{1-8}$ aliphatic chain wherein up to two carbon units of $Z^C$ are optionally and independently replaced by $-CO-$, $-CS-$, $-COCO-$, $-CONR^C-$, $-CONR^C NR^C-$, $-CO_2-$, $-OCO-$, $-NR^C CO_2-$, $-O-$, $-NR^C CONR^C-$, $-OCONR^C-$, $-NR^C NR^C-$, $-NR^C N-R^C CO-$, $-NR^C CO-$, $-S-$, $-SO-$, $-SO_2-$, $-NR^C-$, $-SO_2 NR^C-$, $-NR^C SO_2-$, $-P(O)(OR^C)-$, $-P(O)(OR^C)NR^C-$ or $-NR^C SO_2 NR^C-$; each $R_7$ is independently $R^C$, halo, $-OH$, $-NH_2$, $-NO_2$, $-CN$, $-CF_3$, or $-OCF_3$; and each $R^C$ is independently hydrogen, optionally substituted $C_{1-6}$ aliphatic, optionally substituted cycloaliphatic, optionally substituted heterocycloaliphatic, optionally substituted aryl, or optionally substituted heteroaryl. Alternatively, $R_{4A}$ and $R_{4B}$ together with the carbon atom to which they are attached form a carbonyl group.

In some embodiments, $X_1$ is $-NR_{3A}-$ and $X_2$ is $-CR'_{3A}R'_{3B}-$. For example, $X_1$ is $-NR_{3A}-$ and $X_2$ is $-CR'_{3B}R'_{3C}-$, wherein $R_{3B}$ and $R_{3C}$ together with the carbon atom to which they are attached form a carbonyl group. In another example, $X_1$ is $-NR_{3A}-$ and $X_2$ is $-CR'_{3B}R'_{3C}-$, wherein each of $R'_{3B}$ and $R'_{3C}$ is hydrogen.

In several embodiments, $X_1$ is $-NR_{3A}-$, wherein $R_{3A}$ is $-Z^B R_6$, each $Z^B$ is independently a bond, or an independently and optionally substituted branched or straight $C_{1-6}$ aliphatic chain wherein up to two carbon units of $Z^B$ are optionally and independently replaced by $-CO-$, $-CONR^B-$, $-CO_2-$, $-NR^B CO_2-$, $-SO_2-$, $-O-$, or $-NR^B CO-$, $R_6$ is $R^B$, and each $R^B$ is hydrogen or optionally substituted $C_{1-3}$ aliphatic. For example, $X_1$ is $-NR_{3A}-$, wherein $R_{3A}$ is $-Z^B R_6$, each $Z^B$ is $-CO-$, $-CONH-$, $-CO_2-$, $-NHCO_2-$, $-SO_2-$, $-O-$, or $-NHCO-$, and $R_6$ is hydrogen or optionally substituted $C_{1-3}$ aliphatic. In other examples, $X_1$ is $-NR_{3A}-$, wherein $R_{3A}$ is $Z^B R_6$, $Z^B$ is $-CO-$ or $-CONH-$, and $R_6$ is hydrogen or optionally substituted $C_{1-3}$ aliphatic.

In several embodiments, $X_2$ is $-CR'_{3B}R'_{3C}-$, wherein $R'_{3B}$ and $R'_{3C}$ are each hydrogen, or $R'_{3B}$ and $R'_{3C}$ together with the carbon atom to which they are attached form a carbonyl group.

In other embodiments, $X_1$ is $-NR_{3A}-$, wherein $R_{3A}$ is one selected from hydrogen, aminocarbonyl, methyl, methylcarbonyl, and N,N-dimethylaminocarbonyl; and $X_2$ is $-CR'_{3B}R'_{3C}-$, wherein each of $R'_{3B}$ and $R'_{3C}$ are hydrogen or $R'_{3B}$ and $R'_{3C}$ together with the carbon atom to which they are attached form a carbonyl group.

In other embodiments, $X_3$ is $-CR_{4A}R_{4B}-$, wherein $R_{4A}$ and $R_{4B}$ together with the carbon atom to which they are attached form a carbonyl group, or each of $R_{4A}$ and $R_{4B}$ is hydrogen.

In several embodiments, $X_4$ is $-CR'_{4A}R'_{4B}-$, wherein each of $R'_{4A}$ and $R'_{4B}$ are hydrogen.

3. $R_2$ Group

Each $R_2$ is independently $-Z^A R_5$, wherein each $Z^A$ is independently a bond or is an optionally substituted $C_{1-8}$ aliphatic chain wherein up to two carbon units of $Z^A$ are optionally and independently replaced by $-CO-$, $-CS-$, $-COCO-$, $-CONR^A-$, $-CONR^A NR^A-$, $-CO_2-$, $-OCO-$, $-NR^A CO_2-$, $-O-$, $-NR^A CONR^A-$, $-OCONR^A-$, $-NR^A NR^A-$, $-NR^A NR^A CO-$, $-NR^A CO-$, $-S-$, $-SO-$, $-SO_2-$, $-NR^A-$, $-SO_2 NR^A-$, $-NR^A SO_2-$, $-P(O)(OR^A)-$, $-P(O)(OR^A)NR^A-$ or $-NR^A SO_2 NR^A-$; each $R_5$ is independently $R^A$, halo, $-OH$, —NH₂, —NO₂, —CN, —CF₃, or —OCF₃; and each $R^A$ is independently hydrogen, optionally substituted $C_{1-6}$ aliphatic, optionally substituted cycloaliphatic, optionally substituted heterocycloaliphatic, optionally substituted aryl, or optionally substituted heteroaryl. Alternatively, $R_2$ and one of $R_{3A}$ or $R_{3B}$ together with the atoms to which they are attached form an optionally substituted 4-10 membered heterocyclic or carbocyclic ring.

In several embodiments, $R_2$ is hydrogen or optionally substituted $C_{1-6}$ aliphatic. For example, $R_2$ is an optionally substituted methyl, ethyl, propyl, butyl, ethenyl, propenyl, butenyl, or combinations thereof, each of which is optionally substituted.

4. m n and q groups m is 1-3.

n is 1-3.

q is 0-4.

In several embodiments, m is 1, 2, or 3.

In other embodiments, n is 1, 2, or 3. For example, m+n is 4. In another example, m and n are 2.

In some embodiments, q is 0, 1, 2, 3, or 4. For example, q is 0 or 4.

C. Subgeneric Compounds

Another aspect of the present invention provides compounds useful for modulating the activity of a muscarinic receptor according to formula I-A:

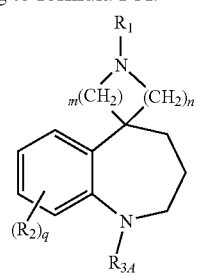

I-A or a pharmaceutically acceptable salt thereof, wherein $R_1$, $R_2$, $R_{3A}$, m, n, and q are define above in formula I.

Another aspect of the present invention provides compounds useful for modulating the activity of a muscarinic receptor according to formula I-B:

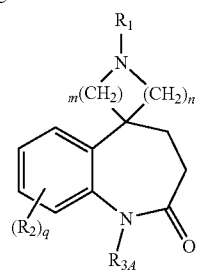

I-B or a pharmaceutically acceptable salt thereof, wherein $R_1$, $R_2$, $R_{3A}$, m, n, and q are define above in formula I.

IV. Combinations of Embodiments

Other embodiments include any combination of the aforementioned substituents $R_1$, $R_2$, $X_1$, $X_2$, $X_3$, $X_4$, m, n, q, and other variables contained therein.

V. Exemplary Compounds

Specific exemplary compounds of formulae (I, I-A, and I-B) are shown below in Table 1.

TABLE 1

Exemplary compounds of formulae (I, I-A, and I-B).

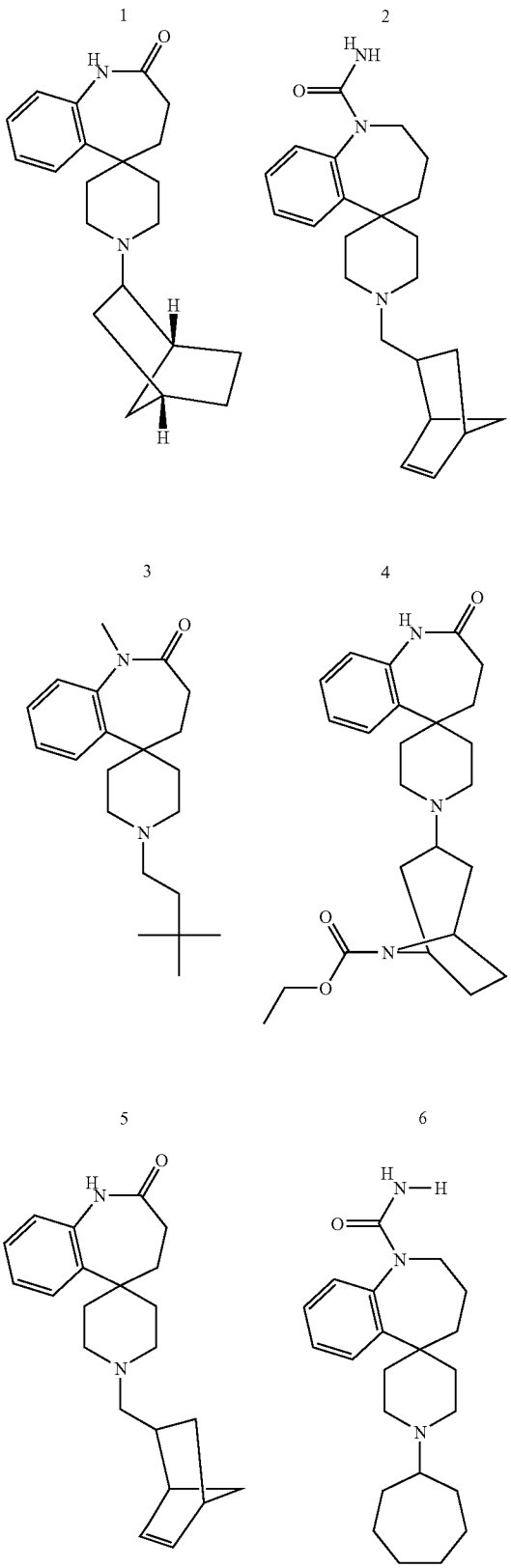

TABLE 1-continued
Exemplary compounds of formulae (I, I-A, and I-B).
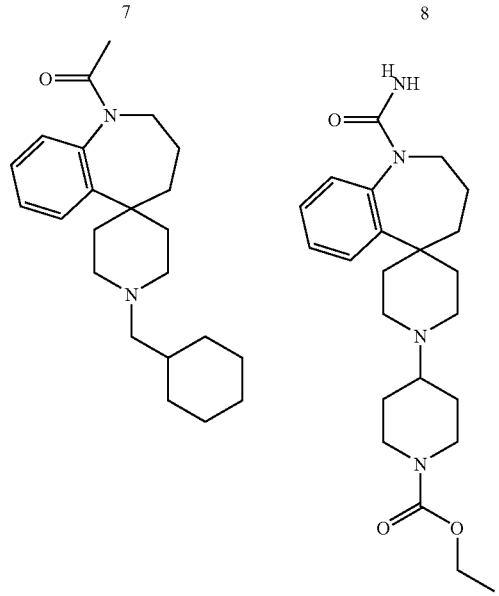
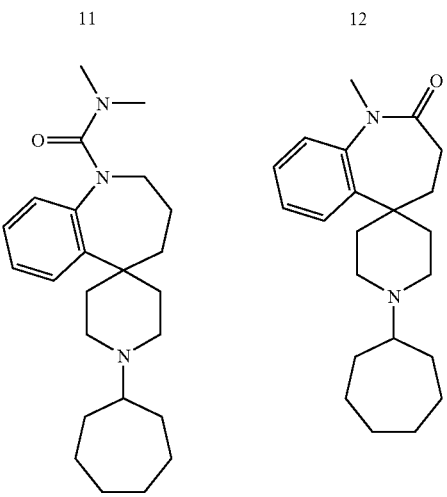
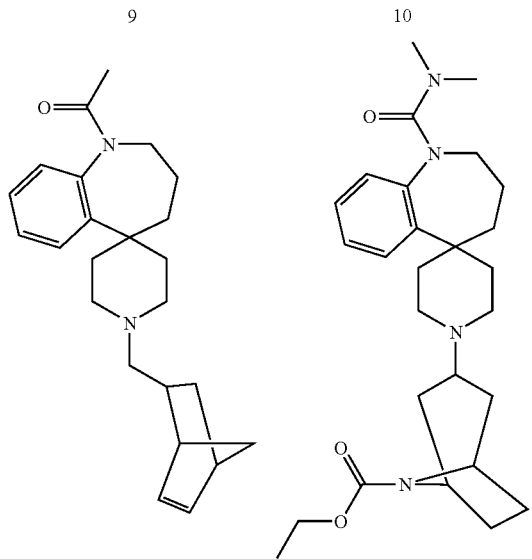

TABLE 1-continued
Exemplary compounds of formulae (I, I-A, and I-B).
| 15 | 16 |
|---|---|
| 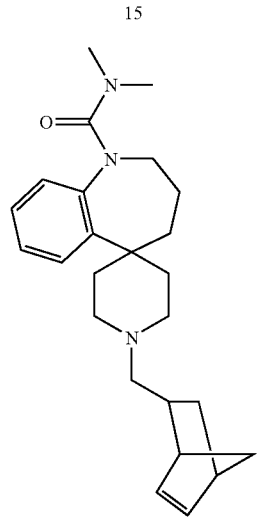 | 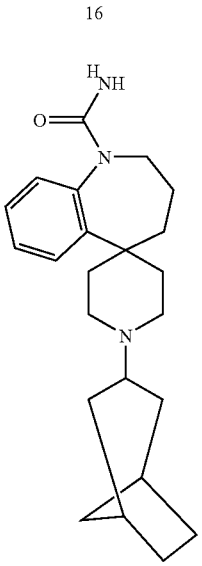 |
| 19 | 20 |
|---|---|
| 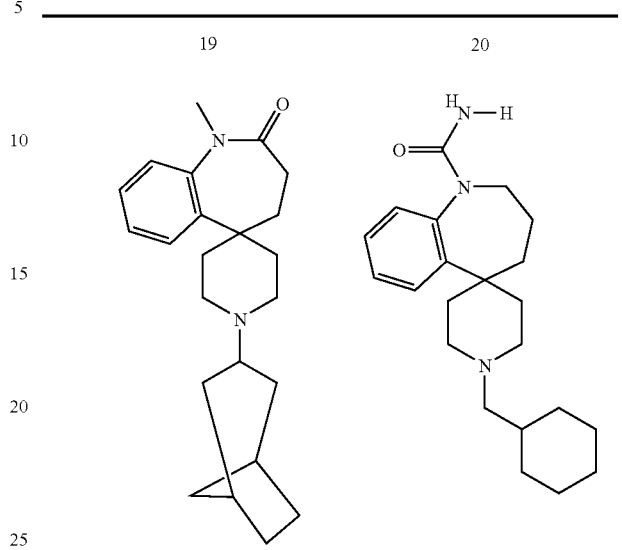 | |
| 17 | 18 |
|---|---|
| 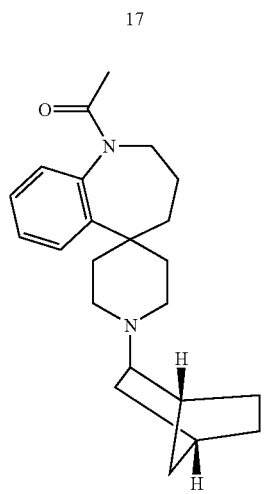 | 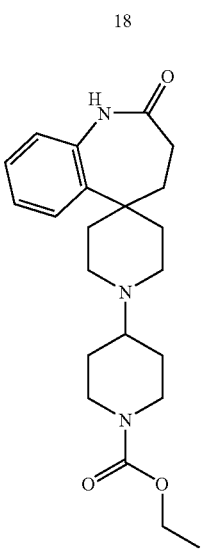 |
| 21 | 22 |
|---|---|
| 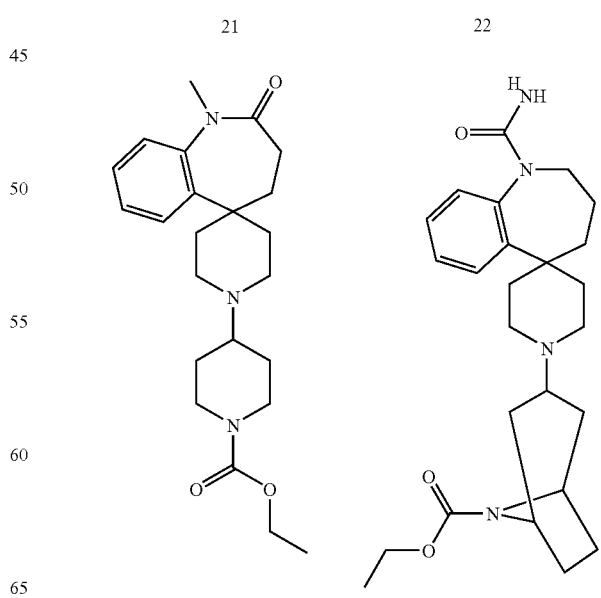 | |

TABLE 1-continued
Exemplary compounds of formulae (I, I-A, and I-B).
| 23 | 24 |
|---|---|
| 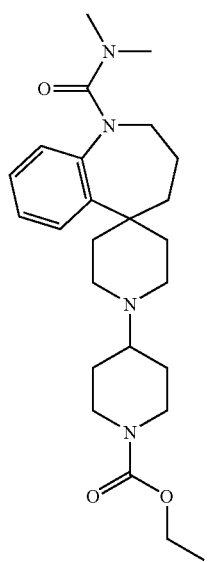 | 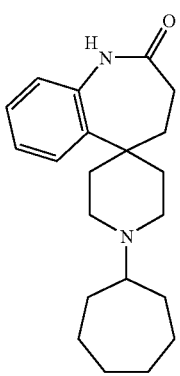 |
| 25 | 26 |
|---|---|
| 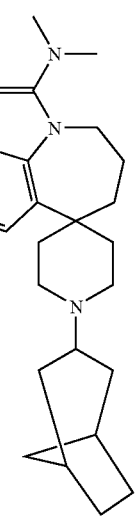 | 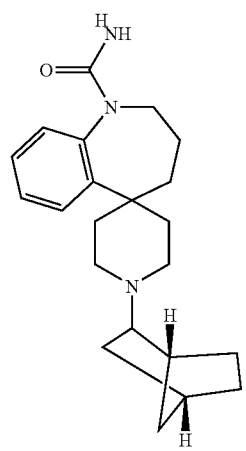 |
TABLE 1-continued
Exemplary compounds of formulae (I, I-A, and I-B).
| 27 | 28 |
|---|---|
| 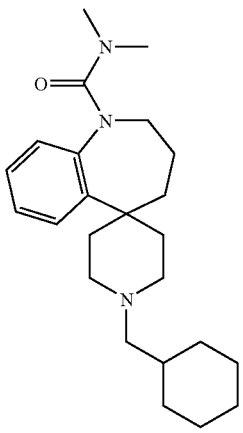 | 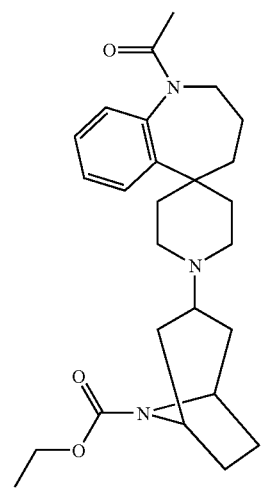 |
| 29 | 30 |
|---|---|
| 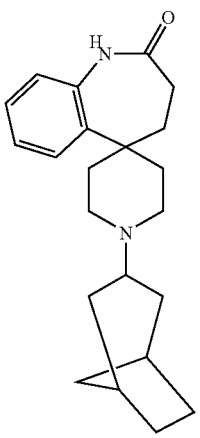 | 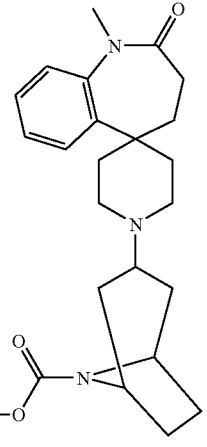 |
| 31 | 32 |
|---|---|
| 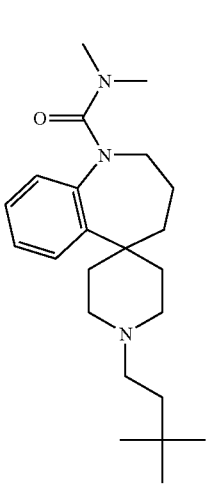 | 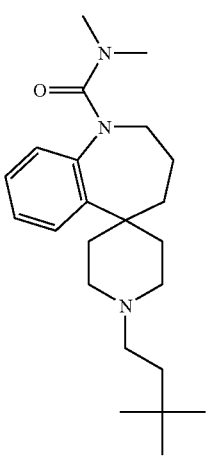 |

TABLE 1-continued

Exemplary compounds of formulae (I, I-A, and I-B).

| 33 | 34 |
| --- | --- |
| 35 | 36 |

VI. Formulations, Administrations, and Uses

The present invention includes within its scope pharmaceutically acceptable prodrugs of the compounds of the present invention. A "pharmaceutically acceptable prodrug" means any pharmaceutically acceptable salt, ester, salt of an ester, or other derivative of a compound of the present invention which, upon administration to a recipient, is capable of providing (directly or indirectly) a compound of this invention or an active metabolite or residue thereof. Preferred prodrugs are those that increase the bioavailability of the compounds of this invention when such compounds are administered to a mammal or which enhance delivery of the parent compound to a biological compartment relative to the parent species.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+$ ($C_{1-4}$ alkyl)$_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the modulator can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

According to a preferred embodiment, the compounds of formulae (I, I-A, and I-B) are selective modulators of $M_1$, $M_2$ and $M_4$. More preferably, the compounds of formulae (I, I-A, and I-B) are effective modulators of $M_1$ and/or $M_4$. Yet more preferably, certain compounds of formulae (I, I-A, I-B) are selective modulators of $M_1$. Or, preferably, certain compounds of formulae (I, I-A, and I-B) are selective modulators of $M_4$.

Applicants believe that the ability of the compounds of the present invention to modulate the activity of muscarinic receptors is derived from the affinity of these compounds to the muscarinic receptors. Such affinity, applicants believe, activates a muscarinic receptor (i.e., an agonist) or inhibits the activity of a muscarinic receptor.

The term "selective" as used herein means a measurably greater ability to modulate one muscarinic receptor subtype when compared to the other muscarinic receptor subtypes. E.g., the term "selective $M_4$ agonist" means a compound that has a measurably greater ability to act as an $M_4$ agonist when compared to that compound's agonist activity with the other muscarinic receptor subtype(s).

According to an alternative embodiment, the present invention provides a method of treating a muscarinic receptor mediated disease in a mammal, such as a human, including the step of administering to said mammal a composition comprising a compound of formulae (I, I-A, and I-B) or an embodiment thereof as set forth herein.

According to another embodiment, the present invention provides a method of treating a disease mediated by a muscarinic receptor including the step of administering to said mammal a composition comprising a compound of formulae (I, I-A, and I-B), or other embodiments thereof as set forth above. Preferably, said disease is mediated by $M_1$, or said disease is mediated by $M_4$.

According to yet another embodiment, the present invention provides a method of treating or reducing the severity of a disease in a patient, wherein said disease is selected from CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, sudden infant death syndrome, Parkinson's disease, peripheral disorders such as reduction of intra ocular-pressure in Glaucoma and treatment of dry eyes and dry mouth including Sjögren's Syndrome, wherein said method comprises the step of contacting said patient with a compound according to the present invention.

According to an alternative embodiment, the present invention provides a method of treating or reducing the severity of a disease in a patient, wherein said disease is selected from pain, psychosis (including schizophrenia, hallucinations, and delusions), Alzheimer's disease, Parkinson's disease, glaucoma, bradycardia, gastric acid secretion, asthma, or GI disturbances.

According to a preferred embodiment, the present invention is useful for treating or reducing the severity of psychosis, Alzheimer's disease, pain, or Parkinson's disease.

All references cited within this document are incorporated herein by reference.

VII. Preparations and Examples

In order that the invention described herein may be more fully understood, the following examples are set forth. It should be understood that these examples are for illustrative purposes only and are not to be construed as limiting this invention in any manner.

Preparation A: Synthesis of 3,4-dihydrospiro[benzo[b]azepine-5,4'-piperidin]-2(1H)-one (E)

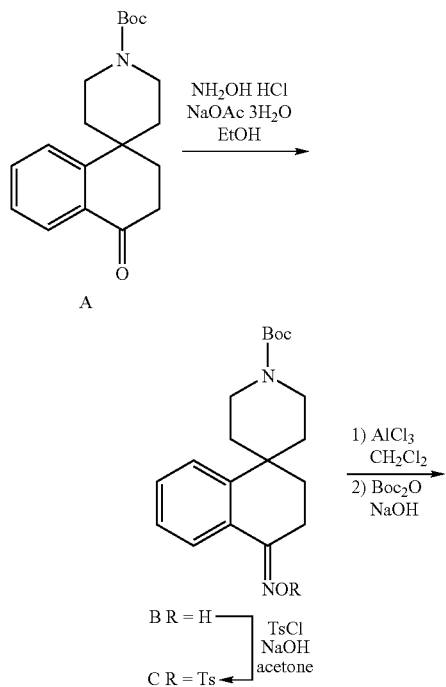

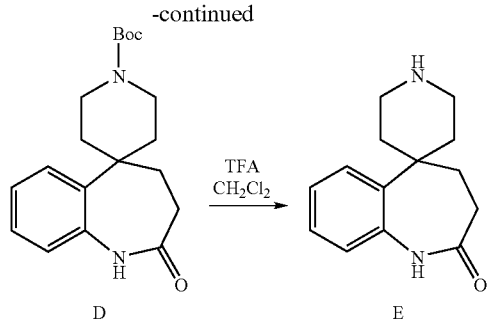

A mixture of tert-butyl 4-oxo-3,4-dihydro-2H-spiro[naphthalene-1,4'-piperidine]-1'-carboxylate A (1.24 g, 3.93 mmol), hydroxylamine hydrochloride (1.37 g, 19.7 mmol) and sodium acetate trihydrate (3.20 g, 23.5 mmol) in ethanol (50 ml) was heated under reflux for 20 h. The reaction was concentrated and the residue was suspended in water, extracted with dichloromethane (3×). The combined extracts were dried over $Na_2SO_4$ and concentrated to give tert-butyl 4-(hydroxyimino)-3,4-dihydro-2H-spiro[naphthalene-1,4'-piperidine]-1'-carboxylate B (1.32 g). LC-MS: m/e=331.1 (M+H, 100%), 275.0 (M+H−C(CH$_3$)$_3$). $R_f$=3.35 min. $^1$H-NMR (500 MHz, CDCl$_3$): 8.01 (d, 0.25H), 7.93 (d, 0.75H), 7.41-7.34 (m, 2H), 7.23-7.19 (m, 1H), 3.95-3.92 (m, 2H), 3.04-2.96 (m, 2H), 2.87 (t, 0.5H), 2.82 (t, 1.5H), 2.3 (br. s, 1H), 1.93-1.84 (m, 4H), 1.54-1.52 (d, 2H), 1.43 (s, 9H).

At 0° C., 6N NaOH (4 ml, 2.4 mmol) was added to a solution of the hydroxyimine B (1.32 g, 4 mmol) and tosyl chloride (840 mg, 4.42 mmol) in acetone (30 ml) and kept at room temperature for 3 h. The reaction mixture was poured into ice, extracted with EtOAc, dried over $Na_2SO_4$, concentrated and purified on silica gel (hexane/EtOAc 9:1 to 7:3) to give tert-butyl 4-(tosyloxyimino)-3,4-dihydro-2H-spiro[naphthalene-1,4'-piperidine]-1'-carboxylate C (1.66 g) in 85% yield as a white solid. LC-MS: m/e=485.1 (M+H), 257.1 (M+H−OTs−C(CH$_3$)$_3$, 100%). $R_f$=4.01 min.

At −78° C., aluminum chloride (1.7 g, 12.7 mmol) was added to a solution of the tosyloxyimine C (1.66 g, 3.43 mmol) in dichloromethane (20 ml) under nitrogen. After the addition, the cooling bath was removed and the reaction mixture was kept at room temperature for 1.5 h. The reaction mixture was cooled with a dry ice-acetone bath, treated with 50% NaOH to pH 11, extracted with dichloromethane (monitored by HPLC). The combined extracts were concentrated and treated with Boc$_2$O (1 g) and triethylamine (3 ml) for 1 h. The mixture was concentrated and purified by flash column chromatography (hexane/EtOAc 8:2 to 7:3) to give tert-butyl 2-oxo-1,2,3,4-tetrahydrospiro[benzo[b]azepine-5,4'-piperidine]-1'-carboxylate D (830 mg) in a 73% yield. LC-MS: m/e=331.0 (M+H), 275.0 (M+H−C(CH$_3$)$_3$, 100%). $R_f$=2.79 min. $^1$H-NMR (500 MHz, DMSO-d$_6$): 9.51 (s, 1H), 7.37 (d, 1H), 7.24 (t, 1H), 7.14 (t, 1H), 6.99 (d, 1H), 3.33 (m, 4H), 2.14-2.10 (m, 4H), 2.10 (dd, J=5.1, 11.3 Hz, H), 1.94-1.89 (m, 2H), 1.86-1.81 (m, 2H), 1.40 (s, 9H). $^1$H NMR (500 MHz, CDCl$_3$): 7.41 (dd, 1H), 7.37 (t, 1H), 7.32 (t, 1H), 7.19 (s, 1H), 6.97 (dd, 1H), 3.54-3.49 (m, 2H), 3.43 (ddd, 2H), 2.38 (t, 2H), 2.21 (t, 2H), 2.10 (ddd, 2H), 1.98-1.94 (m, 2H), 1.46 (s, 9H).

A solution of the Boc-protected benzoazepine (200 mg) in dichloromethane (3 ml) was treated with trifluoroacetic acid (1 ml) for 1 h. The reaction mixture was concentrated, co-evaporated with acetonitrile and dissolved in dichloromethane. The resulting solution was washed with a mixture of brine (ca. 20 ml) and 6N NaOH (1 ml), dried over $Na_2SO_4$ and concentrated to give 3,4-dihydrospiro[benzo[b]azepine-5,4'-piperidin]-2(1H)-one E (139 mg) as a white solid. LC-MS: m/e=231.0 (M+H, 100%). $R_f$=0.79 min.

Preparation B: Synthesis of 1-(3,4-dihydrospiro[benzo[b]azepine-5,4'-piperidine]-1(2H)-yl)ethanone (H)

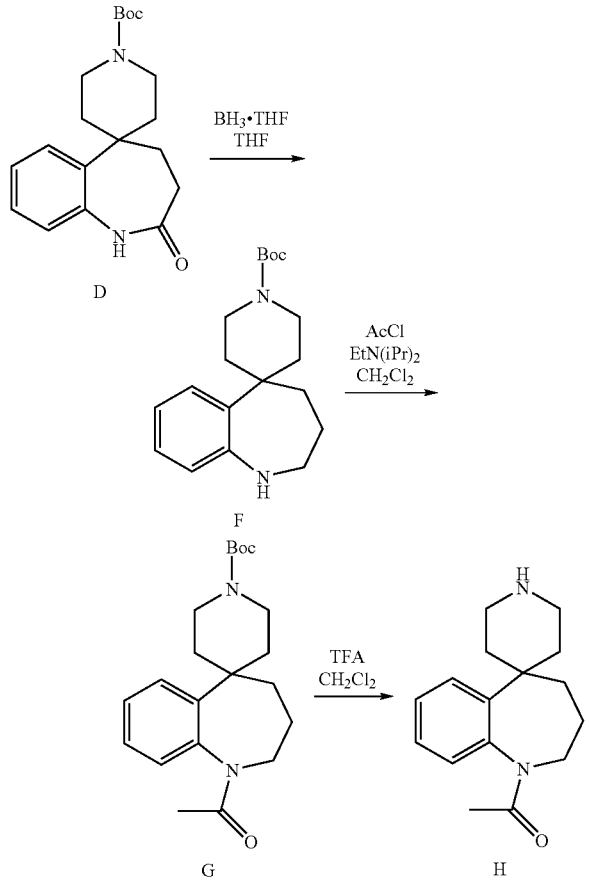

A solution of the 2-oxo-benzo[b]azepine D (560 mg, 1.71 mmol) in THF (20 ml) was heated under reflux with borane-tetrahydrofuran complex (1.0M in THF, 25 ml) for 3 h. Additional borane-tetrahydrofuran complex (11.0M in THF, 10 ml) was added and heated for another 2 h. The reaction mixture was diluted with dichloromethane, washed with 0.5 N HCl (caution! Hydrogen gas was released.). The aqueous phase was basified with 6N NaOH, extracted with dichloromethane. The organic phase was dried ($Na_2SO_4$) concentrated and purified by flash column chromatography ($CH_2Cl_2$) to give tert-butyl 1,2,3,4-tetrahydrospiro[benzo[b]azepine-5,4'-piperidine]-1'-carboxylate F (520 mg) as a colorless oil. LC-MS: m/e=261.0 (M+H−C(CH$_3$)$_3$, 100%). $R_f$=3.05 min. $^1$H-NMR (500 MHz, DMSO-$d_6$): 7.15 (d, 1H), 6.95 (t, 1H), 6.84 (d, 1H), 6.77 (t, 1H), 4.94 (br. s, 1H), 3.47-3.40 (m, 2H), 3.25 (m, 2H), 2.87 (br. s, 2H), 1.97 (m, 2H), 1.89-1.84 (m, 2H), 1.73 (m, 2H), 1.67-1.65 (m, 2H), 1.40 (s, 9H), 2-1.26 (m, 9H).

The dimethylcarbamate J (see below) failed to be synthesized by the treatment with dimethylcarbamyl chloride (1.5-4 equivalent) with the azepine F (180 mg) in the presence of Hunig's base (3 equivalent) or sodium hydride (3 equivalent) under reflux in THF and HMPA. The mixture was treated with acetyl chloride (0.14 ml, 1 mmol) to give tert-butyl 1-acetyl-1,2,3,4-tetrahydrospiro[benzo[b]azepine-5,4'-piperidine]-1'-carboxylate G (257 mg, crude). LC-MS: m/e=359.1 (M+H, 100%), 303.1 (M+H−C(CH$_3$)$_3$). $R_f$=3.27 min. $^1$H NMR (500 MHz, CDCl$_3$): 7.32 (d, 1H), 7.26 (td, 1H), 7.2 (m, 1H), 7.02 (dd, 1H), 4.67 (br. d, 1H), 3.85-3.82 (m, 1H), 3.38-3.31 (m, H). 3.09 (s, H), 3.05 (d, J=2.8 Hz, H), 2.99 (s, H), 2.92 (d, J=9.0 Hz, H), 2.84 (s, H), 2.77 (s, H), 2.67 (dd, J=2.4, 9.7 Hz, H), 2.59 (s, H), 2.56 (s, H), 2.52 (d, J=11.7 Hz, H), 2.23 (s, H), 2.20-2.14 (m, H), 2.09-2.02 (m, H), 1.93-1.90 (m, H), 1.85 (d, J=2.3 Hz, H), 1.63 (s, H), 1.60-1.55 (m, H), 1.42 (s, H), 1.39-1.35 (m, H), 1.32 (s, H), 1.30 (s, H), 1.19 (s, H), A solution of the Boc-protected piperidine G (257 mg) in dichloromethane (5 ml) was treated with TFA (1 ml) to give 1-(3,4-dihydrospiro[benzo[b]azepine-5,4'-piperidine]-1(2H)-yl)ethanone (180 mg) after workup as for the conversion of compound D to E. LC-MS: m/e=259.0 (M+H)$_3$, 100%). $R_f$=1.35 min.

Preparation C: Synthesis of N,N-dimethyl-3,4-dihydrospiro[benzo[b]azepine-5,4'-piperidine]-1(2H)-carboxamide (K) and 3,4-dihydrospiro[benzo[b]azepine-5,4'-piperidine]-1(2H)-carboxamide (M)

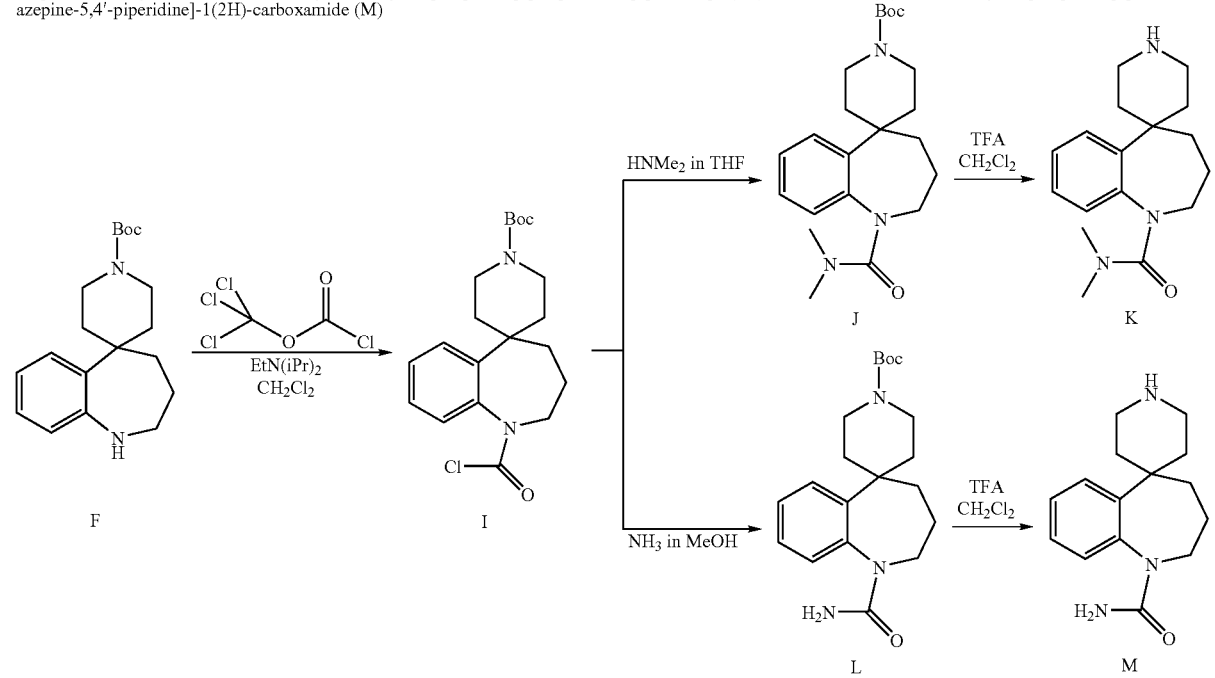

At 0° C., a solution of diphosgene (340 mg, 1.71 mmol) in dichloromethane (5 ml) was added to a solution of the azepine F (415 mg, 1.31 mmol) and ethyldiisopropylamine (0.6 ml, 3.44 mmol). After addition, the reaction mixture was kept at room temperature for 3 hours. The reaction mixture was equally divided into two parts.

One portion was treated with 2.0M dimethylamine in THF (5 ml, 10 mmol) overnight (15 h). After evaporation, the residue was dissolved in dichloromethane, washed with brine. The organic phase was dried and concentrated to give tert-butyl 1-(dimethylcarbamoyl)-1,2,3,4-tetrahydrospiro[benzo[b]azepine-5,4'-piperidine]-1'-carboxylate J (crude, 278 mg). LC-MS: m/e=338.1 (M+1), 332.1 (M+H−C(CH$_3$)$_3$, 100%). $R_t$=3.50 min. The Boc-protected N,N-dimethyl carboxamide J (278 mg) was treated with TFA (1 ml) in dichloromethane (5 ml) for 1 h and workup as for the preparation of H, N,N-dimethyl-3,4-dihydrospiro[benzo[b]azepine-5,4'-piperidine]-1(2H)-carboxamide K (169 mg) was obtained as a white solid. LC-MS: m/e=288.1 (M+1, 100%). $R_t$=1.39 min A second portion was dissolved in MeOH (10 ml) and ammonia gas was bubbled through for 10 min. The reaction mixture was stirred for 3 h. Workup as above to give tert-butyl 1-carbamoyl-1,2,3,4-tetrahydrospiro[benzo[b]azepine-5,4'-piperidine]-1'-carboxylate L (crude, 480 mg). LC-MS: m/e=360.1 (M+1), 304.0 (M+H−C(CH$_3$)$_3$, 100%). $R_t$=2.88 min. Treatment of the Boc-protected carboxamide L (480 mg) with TFA (1 ml) in dichloromethane (5 ml) for 1 h and workup as for the preparation of H from 7, 3,4-dihydrospiro[benzo[b]azepine-5,4'-piperidine]-1(2H)-carboxamide M (270 mg) was obtained as a white solid. LC-MS: m/e=260.1 (M+1, 100%). $R_t$=1.02 min Preparation D: Synthesis of 1-methyl-3,4-dihydrospiro[benzo[b]azepine-5,4'-piperidin]-2(1H)-one (O)

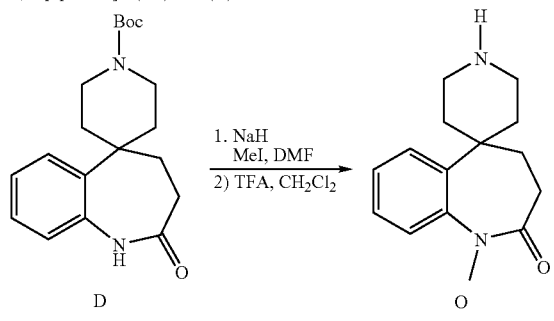

To a solution of tert-butyl 2-oxo-1,2,3,4-tetrahydrospiro[benzo[b]azepine-5,4'-piperidine]-1'-carboxylate D (0.51 g, 1.54 mmol) in DMF at 0° C. was added NaH (60% dispersion in hexanes (130 mg, 3.2 mmol, 2 eq) followed by MeI (0.19 mL, 3.0 mmol, 2 eq). The reaction was warmed to RT and stirred for 3 d. The reaction was diluted with EtOAc and washed with 50% NaHCO$_3$ (2×) and brine. The organics were dried over Na$_2$SO$_4$, filtered and evaporated to give a yellow oil (595 mg) which was used directly in the next step.

The crude product (1.54 mmol) was dissolved in CH$_2$Cl$_2$ and TFA was added and the reaction was stirred at RT for 2 h. The solvent was removed in vacuo and the product azeotroped with CH$_2$Cl$_2$ (3×). The product was dissolved in CH$_2$Cl$_2$ and washed with 1N NaOH, to afford upon drying 0 as a yellow oil (0.463 g, quantitative). FIA m/e=245.4

Reductive Amination

Method I: Reductive amination with aldehydes

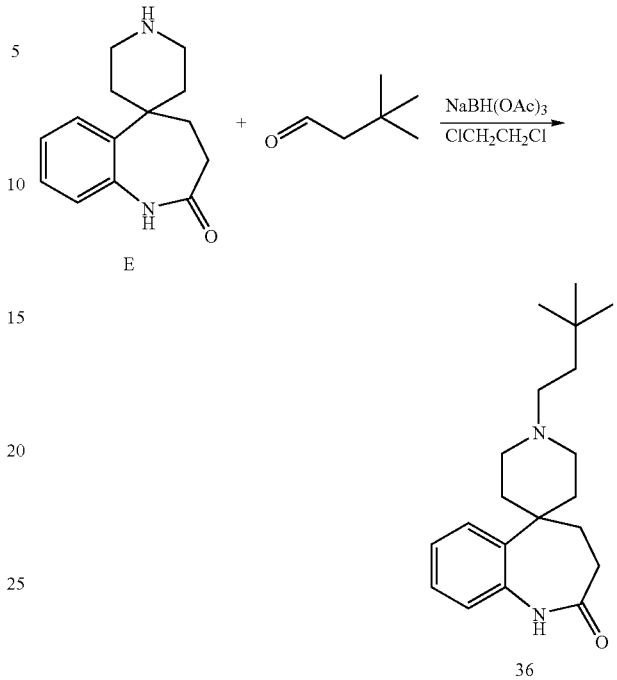

A solution of 3,4-dihydrospiro[benzo[b]azepine-5,4'-piperidin]-2(1H)-one E (20 mg) and 3,3-dimethylbutanal (20 mg) in 1,2-dichloroethane (2 ml) was stirred at 40° C. for 3 h, treated with sodium triacetoxyborohydride (55 mg) for 1 h, cooled to room temperature and MeOH (1 ml) and acetic acid (0.1 ml) was added and stirred for 1 h. After evaporation, the residue was dissolved in MeOH (1 ml) and purified by reverse phase HPLC to give 1'-(3,3-dimethylbutyl)-3,4-dihydrospiro[benzo[b]azepine-5,4'-piperidin]-2(1H)-one 36 as a TFA salt. LC-MS: m/e=315.1 (M+H, 100%). $R_t$=1.61 min.

Method II: Reductive Amination with ketones

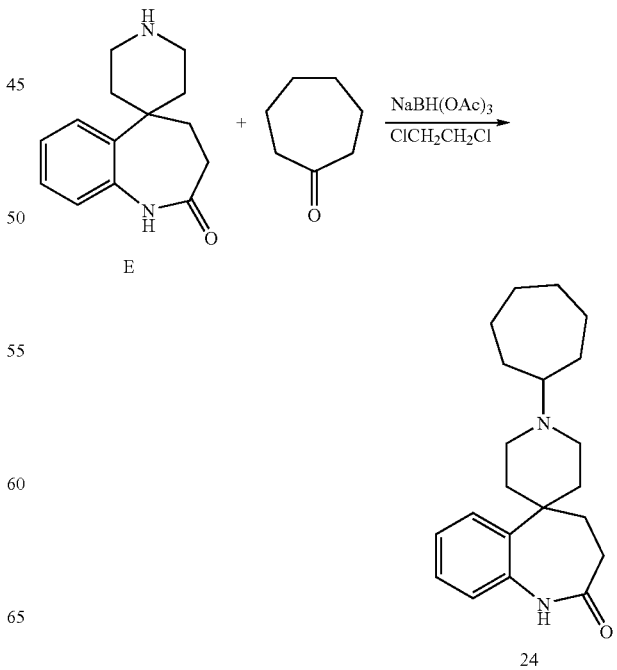

To a solution of 3,4-dihydrospiro[benzo[b]azepine-5,4'-piperidin]-2(1H)-one E (800 mg, 3.47 mmol) and cycloheptanone (1.12 g, 10 mmol) in 1,2-dichloroethane (25 ml) was added titanium tetraisopropoxide (2.5 ml, 8.8 mmol) and the resulting solution was stirred at 40° C. for 15 h, treated with sodium triacetoxyborohydride (2.12 g, 10 mmol) for 1 h, cooled to room temperature and MeOH (1 ml) was added and stirred for 1 h. After evaporation, the residue was dissolved in dichloromethane, washed with a mixture of brine and 6N NaOH (3 ml). The aqueous phase (suspension) was extracted with dichloromethane (3×). The extracts were dried over $Na_2SO_4$, concentrated and purified by silica gel chromatography ($CH_2Cl_2$/MeOH 9:1 to 8:2) to give 1'-cycloheptyl-3,4-dihydrospiro[benzo[b]azepine-5,4'-piperidin]-2(1H)-one (800 mg). LC-MS: m/e=327.1 (M+H, 100%). $R_t$=1.57 min. $^1$H-NMR (500 MHz, DMSO (d6)): 9.46 (s, 1H), 7.37 (d, 1H), 7.20 (t, 1H), 7.12 (t, 1H), 6.95 (d, 1H), 2.51 (m, 2H), 2.44-2.35 (m, 3H), 2.08 (t, 2H), 2.01 (t, 2H), 1.94 (m, 2H), 1.86 (m, 2H), 1.66 (m, 2H), 1.58 (m, 2H), 1.49-1.39 (m, 6H), 1.35-1.29 (m, 2H). The above product was suspended in water, filtration and the solid was dissolved in a diluted 1N HCl (6 ml), lyophilized to give a HCl salt 24 (723 mg). Two conformers were observed with ca. 1:2 ratios. $^1$H-NMR (500 MHz, DMSO-$d_6$): 10.03 (m, 1H); 9.61, 9.57 (2s, 1H); 7.42 (d, 0.35H), 7.38 (d, 0.65H); 7.31, 7.26 (2t, 1H); 7.21, 7.16 (2t, 1H); 7.05, 7.01 (2t, 1H); 3.29 (d, 2H), 3.21 (q, 2H), 2.73 (d, 0.7H), 2.28 (d, 1.3H), 2.63-2.57 (m, 1H), 2.22-1.98 (m, 8H), 1.89-1.84 (m, 1H), 1.73-1.60 (m, 3H), 1.55-1.33 (m, 7H).

Method III: Reductive amination with ketones

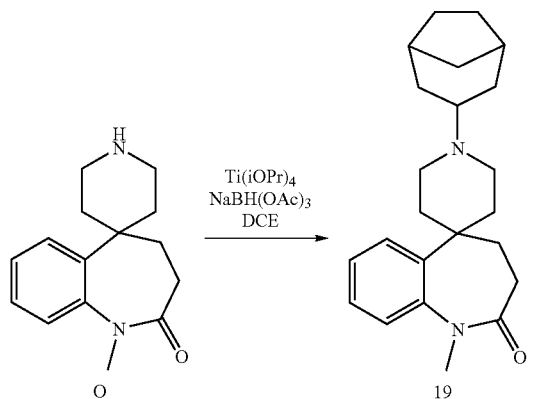

A solution of 1-methyl-3,4-dihydrospiro[benzo[b]azepine-5,4'-piperidin]-2(1H)-one O 60 mg) and bicyclo[3.2.1.]octan-3-one (20 mg) in 1,2-dichloroethane (3 ml) was, treated with sodium triacetoxyborohydride (110 mg, 0.52 mmol) and titanium tetraisopropoxide (0.16 mL, 0.54 mmol) and the reaction was stirred at RT for 5 d. MeOH (1 ml) and 1N NaOH (0.5 ml) were added and the reaction was stirred for 1 h. The mixture was diluted with EtOAc (5 mL) and centrifuged. The organics were decanted, evaporated, then the residue was dissolved in MeOH (1 ml) and purified by reverse phase HPLC to give 1'-(bicyclo[3.2.1.]octan-3-yl)-1-methyl-3,4-dihydrospiro[benzo[b]azepine-5,4'-piperidin]-2(1H)-one (19) as a TFA salt. LC-MS: m/e=426.4 (M+H). $R_t$=1.9 min.

Table 2 below illustrates synthetic methods used to produce exemplary compounds of formula I.

TABLE 2

Methods used to produce exemplary compounds of formula I.

| Comp No. | Preparation method |
|---|---|
| 1 | II |
| 3 | II |
| 4 | II |
| 5 | I |
| 12 | II |
| 18 | II |
| 19 | III |
| 21 | II |
| 24 | II |
| 29 | II |
| 30 | III |
| 35 | II |
| 36 | I |

Analytical data for selected compounds of the present invention is shown below in Table 3.

TABLE 3

| Comp No. | LCMS M + 1 | LC RT (min) |
|---|---|---|
| 1 | 325. | 1.46 |
| 2 | 366.2 | 1.61 |
| 3 | 329.5 | 2.3 |
| 4 | 412.2 | 1.53 |
| 5 | 337.1 | 1.61 |
| 6 | 356.3 | 1.61 |
| 7 | 355.2 | 1.76 |
| 8 | 415.2 | 1.61 |
| 9 | 365.2 | 1.72 |
| 10 | 469.3 | 1.72 |
| 11 | 384.3 | 1.79 |
| 12 | 341.5 | 2.37 |
| 13 | 344.1 | 1.61 |
| 14 | 414.3 | 1.57 |
| 15 | 394.2 | 1.77 |
| 16 | 368.2 | 1.65 |
| 17 | 353.2 | 1.61 |
| 18 | 386.1 | 1.46 |
| 19 | 353.4 | 1.9 |
| 20 | 356.2 | 1.65 |
| 21 | 400.4 | 2.2 |
| 22 | 441.3 | 1.58 |
| 23 | 443.2 | 1.65 |
| 24 | 327.1 | 1.57 |
| 25 | 396.3 | 1.83 |
| 26 | 354.2 | 1.5 |
| 27 | 384.2 | 1.81 |
| 28 | 440.2 | 1.65 |
| 29 | 339.1 | 1.61 |
| 30 | 426.4 | 1.95 |
| 31 | 372.3 | 1.79 |
| 32 | 343.1 | 1.74 |
| 33 | 382.3 | 1.68 |
| 34 | 329.1 | 1.64 |
| 35 | 339.5 | 2.3 |
| 36 | 315.1 | 1.61 |

VIII. Assays for Detecting and Measuring Inhibition Properties of Compounds

Functional Mobilization of Intracellular Calcium to Determine Muscarinic Receptor Activity:

CHO cells expressing muscarinic receptors ($M_1$ to $M_5$) are grown as monolayers in tissue culture flasks at 37° C. in a humidified atmosphere containing 5% $CO_2$ and passaged every 3-5 days. The growth media is Dulbecco's modified eagles medium (DMEM, Gibco Cat#12430-054), containing 25 mM Hepes and supplemented with Fetal Bovine Serum (Hyclone, Cat#SH30071.03), 0.1 mM of MEM non-essential amino acids (GIBCO, Cat#11140-050), 1 mM MEM Sodium Pyruvate (GIBCO Cat#11360-070) and 100 units/ml of Penicillin G and 100 µg/ml of Streptomycin (GIBCO Cat#15140-122). The recombinant muscarinic receptor cell lines are grown under antibiotic pressure with media containing 25 µg/ml zeocin and 500 µg/ml G418 (M1-CHO), 4 µg/ml puromycin, 50 µg/ml zeocin and 2.5 µg/ml blasticidin (M2 and M4-CHO) or 50 µg/ml zeocin and 4 µg/ml puromycin (M3 and M5-CHO).

Cells are harvested at 80-90% confluence using Versene (GIBCO Cat#15040-066), collected by centrifugation and seeded 18-24 hours prior to running the calcium assay at a density of 5,000-10,000 cells/well in back-walled, clear-bottomed 384-well plates (BD Biocoat, poly-D-lysine, Cat#356663). The day of the experiment, the cells are washed with a plate washer (Bioteck Instruments, ELX 405) using bath 1 buffer (140-mM NaCl, 4.5-mM KCl, 2-mM $CaCl_2$, 1-mM $MgCl_2$, 10-mM Hepes-Na, 10-mM Glucose, pH 7.4, with NaOH) containing 1 mM Probenecid. Next, the calcium dye Fluo-3 (25 µl well of Fluo-3 AM at 4 µM, Molecular Probes F-1241, in Bath 1 buffer containing 1 mM Probenecid) is added to the 25 µl of Bath 1 remaining in each well after the plate wash and the dye is loaded at 37° C. in the tissue culture incubator for 60-90 min. The fluorescent dye is removed using the plate washer with Bath 1 containing 1 mM Probenecid, leaving 25 µl/well of this solution after the wash. Alternatively, cells can be loaded with the calcium indicator from Molecular Devices (Calcium 3 Assay Reagents, Cat #R7181) adding 5 µl of a 5× solution dye in Bath 1 containing 1 mM Probenecid (10 ml per dye flask cat#R7182 to generate a solution 20×) to 20 µl of the same buffer. After loading for 60 min, the experiment can be run without having to remove the dye.

Compounds are prepared at a 2× fold concentration in a 96-well plate (round bottom, Costar Corning cat#3656), by reconstituting the pre-spotted compounds in bath 1 containing 1 mM probenecid. The final concentration DMSO is 0.5%, and the amount of DMSO is normalized across the assay plate. To determine an agonist action of the compounds on muscarinic receptors, the reconstituted compounds are added (25 µl compound/well) to the cell assay plate (containing 25 µl/well) using the multi-channel robotic system of the FLIPR 3 Instrument (Molecular Devices, Sunnyvale, Calif.). To determine a functional inhibitory action of the compounds on muscarinic receptors, the reconstituted compounds are added (25 µl compound/well) to the assay plate and pre-incubated for 15 min prior to adding 25 µl of Carbachol at 3× the EC80 for each muscarinic subtype. Alternatively, the compounds can be co-applied simultaneously with the agonist. In both assay modes, the fluorescence is recorded for 60 sec (excitation wavelength is 488 nM and emission wavelength 540 nm) using the FLIPR 3 instrument.

The potency, efficacy and selectivity of the muscarinic compounds were evaluated by screening the compound activity across the whole family ($M_1$ to $M_5$ cells). Compounds were also screened for activity on other proteins such as other GPCRs and ion channels to determine selectivity on $M_4$ receptors.

The compounds of the present invention were found to modulate the $M_1$ and/or $M_4$ muscarinic receptors selectively over the other receptor types.

Examples of activities and efficacies of the muscarinic compounds of formulae (I, I-A, and I-B) on modulating $M_1$ and $M_4$ receptors are shown below in Table 4. The compound activity for the $M_1$ and $M_4$ is illustrated with "+++" if activity was measured to be less than 2.0 µM, "++" if activity was measured to be from 2.0 µM to 10.0 µM, "+" if activity was measured to be greater than 10.0 µM, and "−" if no data was available. The efficacy for $M_1$ and $M_4$ modulation is illustrated with "+++" if efficacy was calculated to be greater than 100%, "++" if efficacy was calculated to be from 100% to 25%, "+" if efficacy was calculated to be less than 25%, and "−" if no data was available. It should be noted that 100% efficacy is the maximum response obtained with the Carbachol control.

TABLE 4

Activities and efficacies of compounds of formulae (I, I-A, and I-B).

| Comp No. | $M_1$ Activity | $M_4$ Activity | $M_1$ Efficacy | $M_4$ Efficacy |
| --- | --- | --- | --- | --- |
| 1 | +++ | +++ | +++ | ++ |
| 2 | ++ | +++ | + | ++ |
| 3 | ++ | +++ | ++ | ++ |
| 4 | +++ | +++ | ++ | ++ |
| 5 | ++ | +++ | ++ | ++ |
| 6 | + | + | + | + |
| 7 | + | ++ | + | + |
| 8 | +++ | ++ | ++ | ++ |
| 9 | + | +++ | + | ++ |
| 10 | + | ++ | + | + |
| 11 | + | + | + | + |
| 12 | ++ | +++ | ++ | ++ |
| 13 | ++ | +++ | ++ | ++ |
| 14 | +++ | +++ | ++ | ++ |
| 15 | + | +++ | + | ++ |
| 16 | ++ | +++ | ++ | ++ |
| 17 | + | + | + | + |
| 18 | +++ | +++ | ++ | ++ |
| 19 | +++ | +++ | ++ | ++ |
| 20 | + | ++ | + | + |
| 21 | ++ | ++ | ++ | ++ |
| 22 | +++ | +++ | ++ | ++ |
| 23 | ++ | +++ | ++ | ++ |
| 24 | +++ | +++ | ++ | ++ |
| 25 | + | +++ | + | ++ |
| 26 | + | + | + | + |
| 27 | + | + | + | + |
| 28 | +++ | +++ | ++ | ++ |
| 29 | +++ | +++ | ++ | ++ |
| 30 | +++ | +++ | ++ | ++ |
| 31 | + | +++ | + | ++ |
| 32 | ++ | +++ | + | ++ |
| 33 | + | + | + | + |
| 34 | + | + | + | + |
| 35 | + | +++ | + | ++ |
| 36 | +++ | +++ | ++ | ++ |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of formula I:

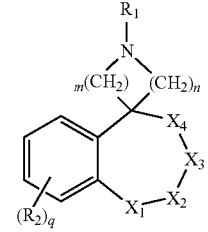

a pharmaceutically acceptable salt thereof, wherein $X_1$ is $-NR_{3A}-$;
$X_2$ is $-CR'_{3B}R'_{3C}-$;
$X_3$ is $-CR_{4A}R_{4B}-$;
$X_4$ is $-CR'_{4A}R'_{4B}-$;
$R_1$ is hydrogen, optionally substituted $C_{1-12}$ aliphatic, optionally substituted cycloaliphatic, or optionally substituted heterocycloaliphatic;
Each $R_2$ is independently $-Z^A R_5$, wherein each $Z^A$ is independently a bond or is an optionally substituted $C_{1-8}$ aliphatic chain wherein up to two carbon units of $Z^A$ are optionally and independently replaced by $-CO-$, $-CS-$, $-COCO-$, $-CONR^A-$, $-CONR^A NR^A-$, $-CO_2-$, $-OCO-$, $-NR^A CO_2-$, $-O-$, $-NR^A CONR^A-$, $-OCONR^A-$, $-NR^A NR^A-$, $-NR^A NR^A CO-$, $-NR^A CO-$, $-S-$, $-SO-$, $-SO_2-$, $-NR^A-$, $-SO_2 NR^A-$, $-NR^A SO_2-$, $-P(O)(OR^A)-$, $-P(O)(OR^A)NR^A-$ or $-NR^A SO_2 NR^A-$,
Each $R_5$ is independently $R^A$, halo, $-OH$, $-NH_2$, $-NO_2$, $-CN$, $-CF_3$, or $-OCF_3$,
Each $R^A$ is independently hydrogen, optionally substituted $C_{1-6}$ aliphatic, optionally substituted cycloaliphatic, optionally substituted heterocycloaliphatic, optionally substituted aryl, or optionally substituted heteroaryl;
Each of $R_{3A}$, $R'_{3B}$, and $R'_{3C}$ is independently $-Z^B R_6$, wherein each $Z^B$ is independently a bond or is an optionally substituted $C_{1-8}$ aliphatic chain wherein up to two carbon units of $Z^B$ are optionally and independently replaced by $-CO-$, $-CS-$, $-COCO-$, $-CONR^B-$, $-CONR^B NR^B-$, $-CO_2-$, $-OCO-$, $-NR^B CO_2-$, $-O-$, $-NR^B CONR^B-$, $-OCONR^B-$, $-NR^B NR^B-$, $-NR^B NR^B CO-$, $-NR^B CO-$, $-S-$, $-SO-$, $-SO_2-$, $-NR^B-$, $-SO_2 NR^B-$, $-NR^B SO_2-$, $-P(O)(OR^B)-$, $-P(O)(OR^B)NR^B-$ or $-NR^B SO_2 NR^B-$,
Each $R_6$ is independently $R^B$, halo, $-OH$, $-NH_2$, $-NO_2$, $-CN$, $-CF_3$, or $-OCF_3$,
Each $R^B$ is independently hydrogen, optionally substituted $C_{1-6}$ aliphatic, optionally substituted cycloaliphatic, optionally substituted heterocycloaliphatic, optionally substituted aryl, or optionally substituted heteroaryl, or
$R'_{3B}$ and $R'_{3C}$ together with the carbon atom to which they are attached form a carbonyl group;
Each of $R_{4A}$, $R'_{4A}$, $R_{4B}$, and $R'_{4B}$ is independently $-Z^C R_7$, wherein each $Z^C$ is independently a bond or is an optionally substituted $C_{1-8}$ aliphatic chain wherein up to two carbon units of $Z^C$ are optionally and independently replaced by $-CO-$, $-CS-$, $-COCO-$, $-CONR^C-$, $-CONR^C NR^C-$, $-CO_2-$, $-OCO-$, $-NR^C CO_2-$, $-O-$, $-NR^C CONR^C-$, $-OCONR^C-$, $-NR^C NR^C-$, $-NR^C NR^C CO-$, $-NR^C CO-$, $-S-$, $-SO-$, $-SO_2-$, $-NR^C-$, $-SO_2 NR^C-$, $-NR^C SO_2-$, $-P(O)(OR^C)-$, $-P(O)(OR^C)NR^C-$ or $-NR^C SO_2 NR^C-$,
Each $R_7$ is independently $R^C$, halo, $-OH$, $-NH_2$, $-NO_2$, $-CN$, $-CF_3$, or $-OCF_3$,
Each $R^C$ is independently hydrogen, optionally substituted $C_{1-6}$ aliphatic, optionally substituted cycloaliphatic, optionally substituted heterocycloaliphatic, optionally substituted aryl, or optionally substituted heteroaryl, or
$R_{4A}$ and $R_{4B}$ together with the carbon atom to which they are attached form a carbonyl group;
m is 1-3;
n is 1-3; and
q is 0-4.

2. The compound of claim 1, wherein $X_1$ is $-NR_{3A}-$ and $X_2$ is $-CR'_{3B}R'_{3C}-$.

3. The compound of claim 2, wherein $X_1$ is $-NR_{3A}-$ and $X_2$ is $-CR'_{3B}R'_{3C}-$, wherein $R_{3B}$ and $R_{3C}$ together with the carbon atom to which they are attached form a carbonyl group.

4. The compound of claim 1, wherein $X_1$ is $-NR_{3A}-$ and $X_2$ is $-CR'_{3B}R'_{3C}-$, wherein each of $R'_{3B}$ and $R'_{3C}$ is hydrogen.

5. The compound of claim 1, wherein $R_1$ is an optionally substituted $C_{1-12}$ aliphatic.

6. The compound of claim 5, wherein $R_1$ is an optionally substituted group selected from $C_{1-12}$ alkyl, $C_{1-12}$ alkenyl, or $C_{1-12}$ alkynyl.

7. The compound of claim 6, wherein $R_1$ is an optionally substituted $C_{1-6}$ alkyl.

8. The compound of claim 7, wherein $R_1$ is selected from methyl, ethyl, n-propyl, isopropyl, n-butyl, sec-butyl, t-butyl, hexyl, 3,3-dimethylbutyl, or 3-methylbutyl, each of which is optionally substituted.

9. The compound of claim 1, wherein $R_1$ is an optionally substituted cycloaliphatic.

10. The compound of claim 9, wherein $R_1$ is an optionally substituted monocyclic cycloaliphatic or an optionally substituted bicyclic cycloaliphatic.

11. The compound of claim 10, wherein $R_1$ is an optionally substituted 3-9 membered monocyclic cycloaliphatic.

12. The compound of claim 11, wherein $R_1$ is cyclopropyl, cyclobutyl, cyclopentyl, cyclohexyl, cycloheptyl, or cyclooctyl, each of which is optionally substituted with halo, hydroxy, aliphatic, amino, carboxy, cycloaliphatic, heterocycloaliphatic, aryl, or heteroaryl.

13. The compound of claim 10, wherein $R_1$ is an optionally substituted 7-10 membered bicyclic cycloaliphatic.

14. The compound of claim 13, wherein $R_1$ is an optionally substituted 7-10 membered bicyclic cycloalkyl or an optionally substituted 7-10 membered bicyclic cycloalkenyl.

15. The compound of claim 14, wherein $R_1$ is an optionally substituted group selected from bicyclo[2.1.1]hexane-yl, bicyclo[2.2.1]heptane-yl, bicyclo[2.2.2]octane, bicyclo[3.1.1]heptane, bicyclo[3.2.1]octane-yl, or bicyclo[3.3.1]nonane-yl, bicyclo[2.1.1]hex-2-ene-yl, bicyclo[2.2.1]hept-2-ene-yl, and bicyclo[2.2.2]oct-2-ene-yl.

16. The compound of claim 1, wherein $R_1$ is an optionally substituted monocyclic heterocycloaliphatic or an optionally substituted bicyclic heterocycloaliphatic.

17. The compound of claim 16, wherein $R_1$ is an optionally substituted 3-8 membered monocyclic heterocycloaliphatic having 1-3 heteroatoms independently selected from N, O, and S.

18. The compound of claim 17, wherein $R_1$ is a tetrahydrofuran-yl, tetrahydro-2H-thiopyran-yl, pyrrolidine-yl, imidazolidine-yl, 1,4-dioxane-yl, morpholine-yl, piperidine-yl, piperazine-yl, tetrahydro-2H-pyran-yl, pyrazolidine-yl, or thiomorpholine-yl, each of which is optionally substituted with 1-3 of halo, amido, acyl, (heterocycloaliphatic)carbonyl, alkenyloxycarbonyl or combinations thereof.

19. The compound of claim 16, wherein $R_1$ is an optionally substituted 7-10 membered bicyclic heterocycloaliphatic having 1-2 heteroatoms independently selected from N, O, and S.

20. The compound of claim 19, wherein $R_1$ is an optionally substituted 7-10 membered bridged bicyclic heterocycloaliphatic or an optionally substituted 7-10 membered fused bicyclic heterocycloaliphatic.

21. The compound of claim 20, wherein R₁ is 8-azabicyclo[3.2.1]octane-yl, or azabicyclo[2.2.1]heptane-yl, each of which is optionally substituted.

22. The compound of claim 1, wherein R₁ is one selected from bicyclo[2.2.1]heptane-2-yl; bicyclo[2.2.1]hept-2-ene-5-ylmethyl; cycloheptane-yl; cyclohexylmethyl; N-ethoxycarbonylpiperidine-4-yl; 8-ethoxycarbonyl-8-azabicyclo[3.2.1]octane-3-yl; neohexyl; cyclooctane-3-yl; cyclohexylmethyl; and 2-methylbutyl.

23. The compound of claim 1, wherein $R_2$ is hydrogen or optionally substituted $C_{1-6}$ aliphatic.

24. The compound of claim 23, wherein $R_2$ is an optionally substituted methyl, ethyl, propyl, butyl, ethenyl, propenyl, butenyl, or combinations thereof, each of which is optionally substituted.

25. The compound of claim 1, wherein $X_1$ is —NR₃ₐ—, wherein $R_{3A}$ is —$Z^B R_6$, each $Z^B$ is independently a bond, or an independently and optionally substituted branched or straight $C_{1-6}$ aliphatic chain wherein up to two carbon units of $Z^B$ are optionally and independently replaced by —CO—, —CONR^B—, —CO₂—, —NR^B CO₂—, —SO₂—, —O—, or —NR^B CO—, $R_6$ is $R^B$, and each $R^B$ is hydrogen or optionally substituted $C_{1-3}$ aliphatic.

26. The compound of claim 1, wherein $X_2$ is —CR'₃ᵦR'₃c—, wherein R'₃ᵦ and R'₃c are each hydrogen, or R'₃ᵦ and R'₃c together with the carbon atom to which they are attached form a carbonyl group.

27. The compound of claim 1, wherein $X_1$ is —NR₃ₐ—, wherein $R_{3A}$ is —$Z^B R_6$, each $Z^B$ is —CO—, —CONH—, —CO₂—, —NHCO₂—, —SO₂—, —O—, or —NHCO—, and $R_6$ is hydrogen or optionally substituted $C_{1-3}$ aliphatic.

28. The compound of claim 1, wherein $X_1$ is —NR₃ₐ—, wherein $R_{3A}$ is one selected from hydrogen, aminocarbonyl, methyl, methylcarbonyl, and N,N-dimethylaminocarbonyl; and $X_2$ is —CR'₃ᵦR'₃c—, wherein each of R'₃ᵦ and R'₃c are hydrogen or R'₃ᵦ and R'₃c together with the carbon atom to which they are attached form a carbonyl group.

29. The compound of claim 1, wherein $X_4$ is —CR'₄ₐR'₄ᵦ—, wherein each of R'₄ₐ and R'₄ᵦ are hydrogen.

30. The compound of claim 1, wherein m is 2 and n is 2.

31. The compound of claim 1, wherein q is 0 or 4.

32. A compound selected from

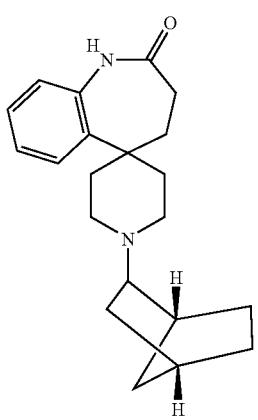
1

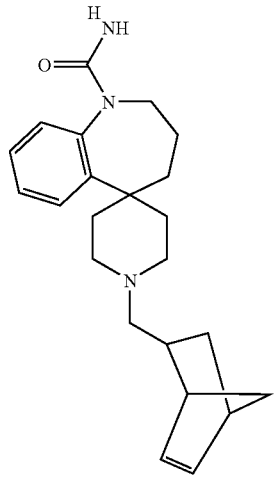
2

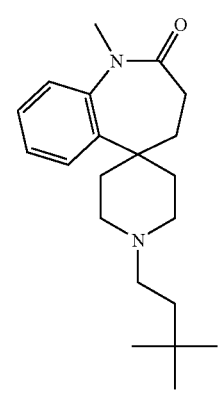
3

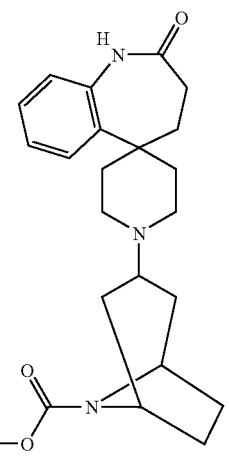
4

-continued
5
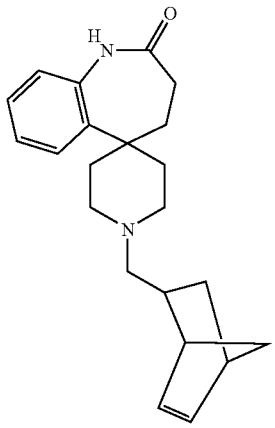
6
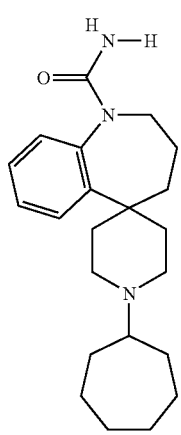
7
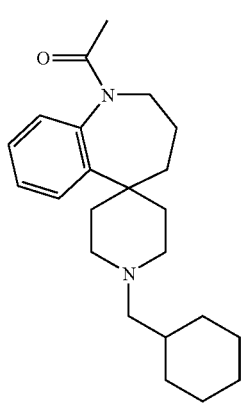
-continued
8
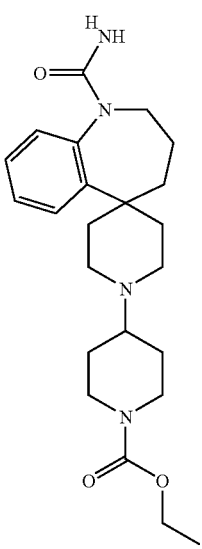
9
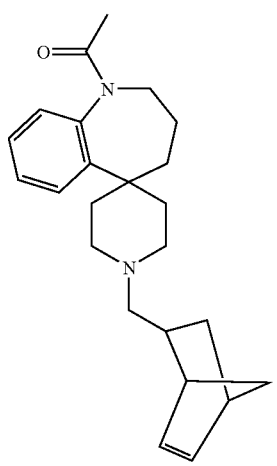
10
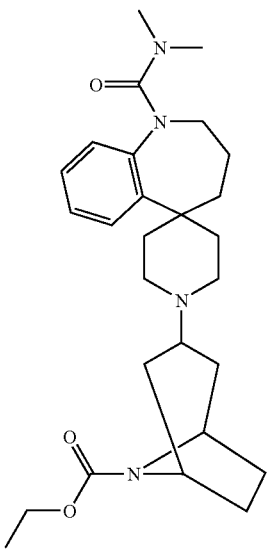

-continued
11
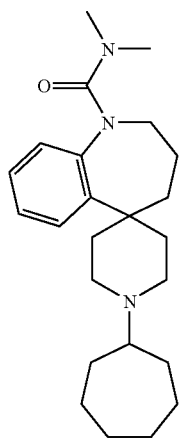
12
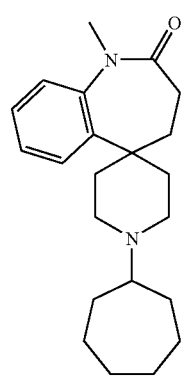
13
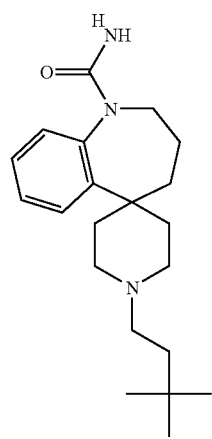
-continued
14
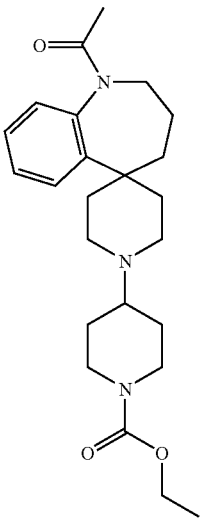
15
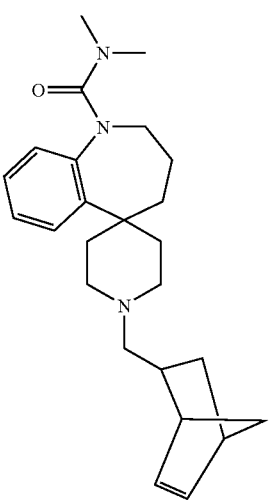
16
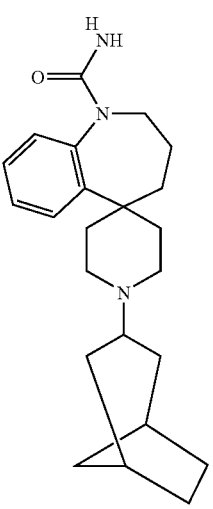

51
-continued
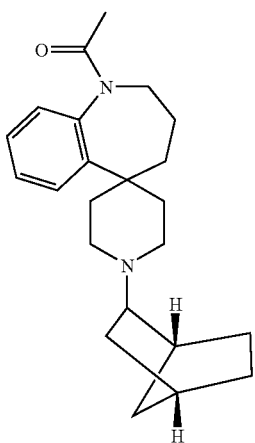
17
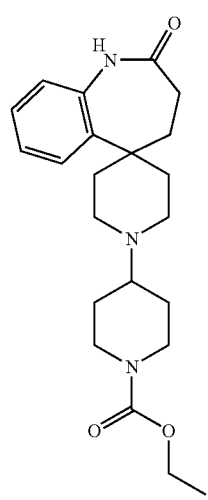
18
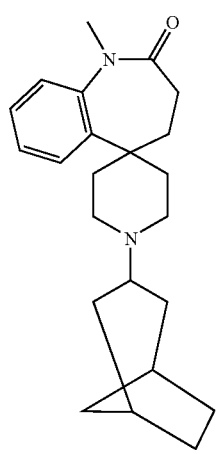
19
52
-continued
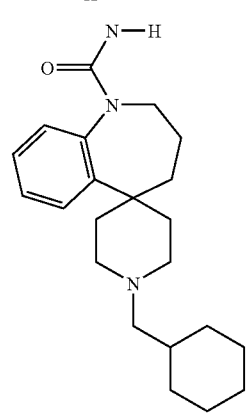
20
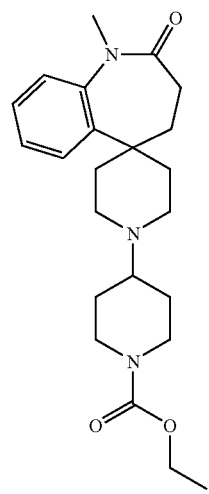
21
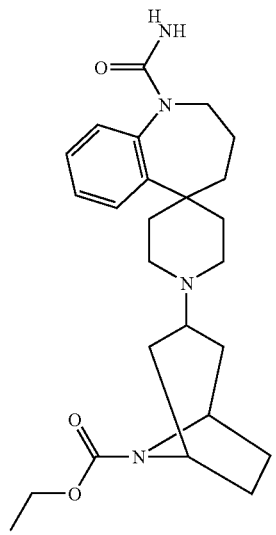
22

23
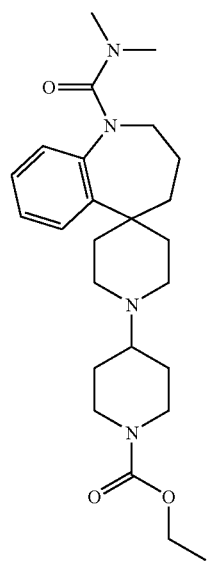
24
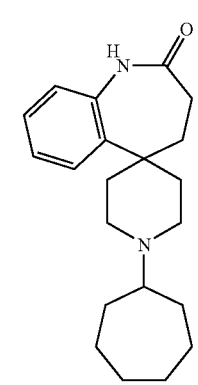
25
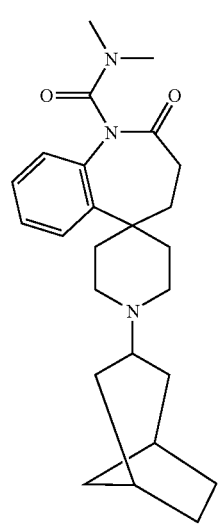
26
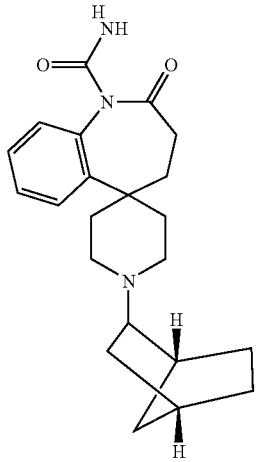
27
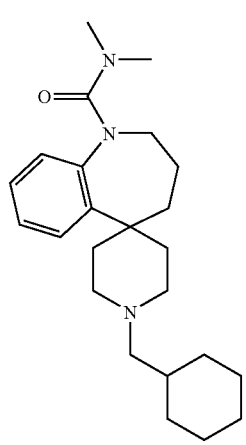
28
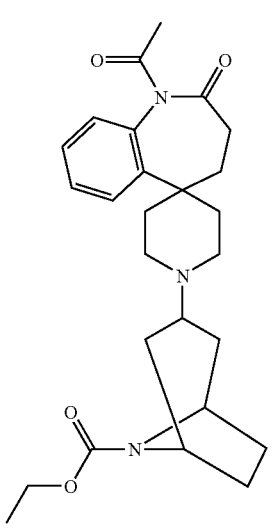

29
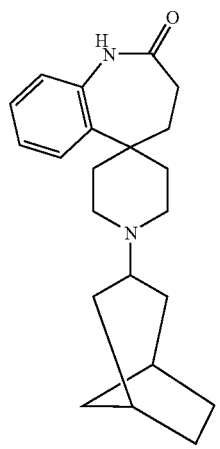
30
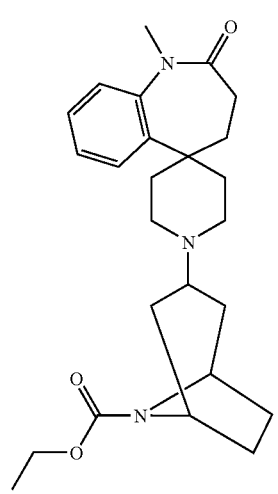
31
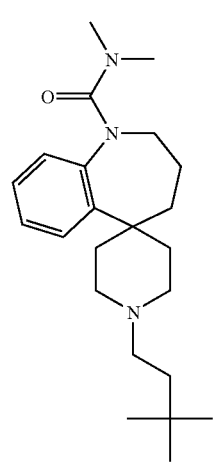
32
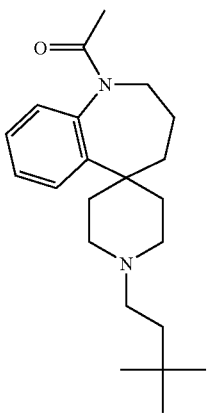
33
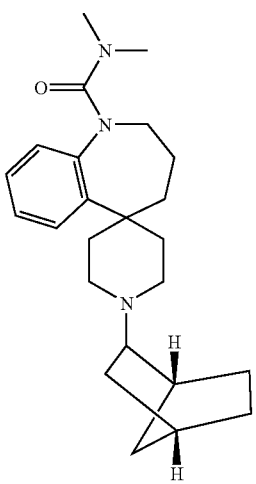
34
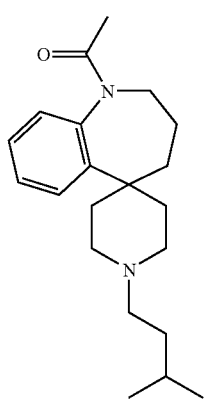

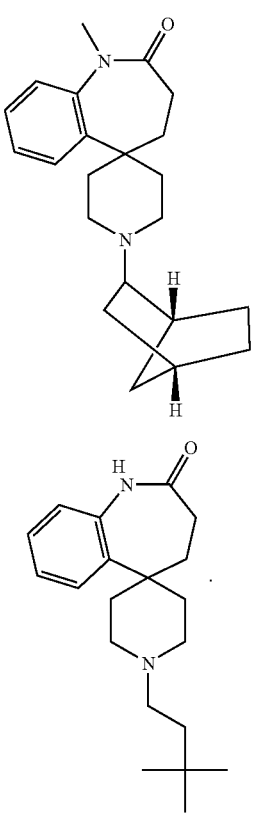

35

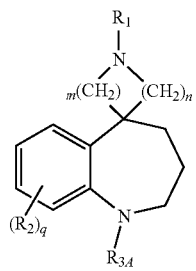

36

33. A pharmaceutical composition comprising a compound according to claim 1 and a pharmaceutically acceptable carrier, adjuvant or vehicle.

34. A compound of formula I-A:

I-A

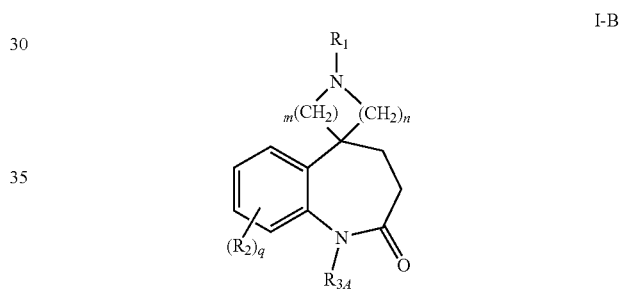

or a pharmaceutically acceptable salt thereof, wherein $R_1$ is a $C_{1-6}$ alkyl which is optionally substituted with a cycloaliphatic, a heterocycloaliphatic, an alkylsulfanyl, an alkoxy, an amino, or combinations thereof; a monocyclic cycloaliphatic or a bicyclic cycloaliphatic which is optionally substituted with 1-3 of halo, aliphatic, hydroxy, alkoxycarbonyl, cycloaliphatic, or combinations thereof; a monocyclic heterocycloaliphatic which is optionally substituted with 1-3 of halo, amido, acyl, (heterocycloaliphatic)carbonyl, alkyloxycarbonyl, alkenyloxycarbonyl or combinations thereof; or a bicyclic heterocycloaliphatic which is optionally substituted with 1-3 of halo, aliphatic, hydroxy, amino, acyl, or combinations thereof;

$R_2$ is hydrogen;

$R_{3A}$ is selected from hydrogen, aminocarbonyl, methyl, methylcarbonyl, and N,N-dimethylaminocarbonyl;

m is 2;

n is 2; and q is 4.

35. The compound of claim 34, wherein $R_1$ is selected from methyl, ethyl, n-propyl, isopropyl, n-butyl, sec-butyl, t-butyl, hexyl, 3,3-dimethylbutyl, or 3-methylbutyl.

36. The compound of claim 34, wherein $R_1$ is one selected from: hydrogen; cyclohexylmethyl; 3,3-dimethylbutyl; bicyclo[2.2.1]hept-5-en-2-yl; cyclohept-1-yl; bicyclo[2.2.1]heptane-2-yl; 1-ethoxycarbonylpiperidine-4-yl; 8-ethoxycarbonyl-8-azabicyclo[3.2.1]octane-3-yl; 3-methylbutyl; (tetrahydro-2H-pyran-4-yl)ethyl; 4-(methyl(sulfanyl))butyl; 3,7-dimethyl-7-methoxyoctyl; (tetrahydro-2H-thiopyran-4-yl)ethyl; cyclohexyl; cycloheptyl; cyclopentyl; (N,N-dimethylaminocarbonyl)piperidine-4-yl; N-acetylpiperidine-4-yl; 1-(cyclopropyl(carbonyl))piperidine-4-yl; (prop-2-ynoxy(carbonyl))piperidine-4-yl; piperidine-4-yl; propoxycarbonylpiperidine-4-yl; (prop-2-enoxy(carbonyl))piperidine-4-yl; (morpholine-4-yl(carbonyl))piperidine-4-yl; and 1-methoxycarbonylpiperidine-4-yl; bicyclo[2.2.1]hept-5-en-2-ylmethyl; and isopropylcarbonylpiperidine-4-yl.

37. A compound according to formula I-B:

I-B or a pharmaceutically acceptable salt thereof, wherein $R_1$ is a $C_{1-6}$ alkyl which is optionally substituted with a cycloaliphatic, a heterocycloaliphatic, an alkylsulfanyl, an alkoxy, an amino, or combinations thereof; a monocyclic cycloaliphatic or a bicyclic cycloaliphatic which is optionally substituted with 1-3 of halo, aliphatic, hydroxy, alkoxycarbonyl, cycloaliphatic, or combinations thereof; a monocyclic heterocycloaliphatic which is optionally substituted with 1-3 of halo, amido, acyl, (heterocycloaliphatic)carbonyl, alkyloxycarbonyl, alkenyloxycarbonyl or combinations thereof; or a bicyclic heterocycloaliphatic which is optionally substituted with 1-3 of halo, aliphatic, hydroxy, amino, acyl, or combinations thereof;

$R_2$ is hydrogen;

$R_{3A}$ is selected from hydrogen, aminocarbonyl, methyl, methylcarbonyl, and N,N-dimethylaminocarbonyl;

m is 2;

n is 2; and q is 4.

38. The compound of claim 37, wherein $R_1$ is selected from methyl, ethyl, n-propyl, isopropyl, n-butyl, sec-butyl, t-butyl, hexyl, 3,3-dimethylbutyl, or 3-methylbutyl.

39. The compound of claim 37, wherein $R_1$ is one selected from: hydrogen; cyclohexylmethyl; 3,3-dimethylbutyl; bicyclo[2.2.1]hept-5-en-2-yl; cyclohept-1-yl; bicyclo[2.2.1]hepttane-2-yl; 1-ethoxycarbonylpiperidine-4-yl; 8-ethoxycarbonyl-8-azabicyclo[3.2.1]octane-3-yl; 3-methylbutyl; (tetrahydro-2H-pyran-4-yl)ethyl; 4-(methyl(sulfanyl))butyl; 3,7-dimethyl-7-methoxyoctyl; (tetrahydro-2H-thiopyran-4-yl)ethyl; cyclohexyl; cycloheptyl; cyclopentyl; (N,N-dimethylaminocarbonyl)piperidine-4-yl; N-acetylpiperidine-4-yl; 1-(cyclopropyl(carbonyl))piperidine-4-yl; (prop-2-ynoxy(carbonyl))piperidine-4-yl; piperidine-4-yl; propoxycarbonylpiperidine-4-yl; (prop-2-enoxy(carbonyl))piperidine-4-yl; (morpholine-4-yl(carbonyl))piperidine-4-yl; and 1-methoxycarbonylpiperidine-4-yl; bicyclo[2.2.1]hept-5-en-2-ylmethyl; and isopropylcarbonylpiperidine-4-yl.

* * * * *